United States Patent
Radons et al.

(10) Patent No.: US 7,179,279 B2
(45) Date of Patent: Feb. 20, 2007

(54) RAPID INDUCTION OF MILD HYPOTHERMIA

(75) Inventors: Stephen W. Radons, Snohomish, WA (US); Larry R. Nygaard, Snohomish, WA (US); Martin S. Abbenhouse, Kirkland, WA (US); Steven M. Chester, Kirkland, WA (US)

(73) Assignee: MedTronic Physio Control Corp., Redmond, WA (US)

( * ) Notice: Subject to any disclaimer, the term of this patent is extended or adjusted under 35 U.S.C. 154(b) by 254 days.

(21) Appl. No.: 10/262,604

(22) Filed: Sep. 30, 2002

(65) Prior Publication Data

US 2004/0064170 A1 Apr. 1, 2004

(51) Int. Cl.
*A61F 7/00* (2006.01)

(52) U.S. Cl. ............... 607/108; 607/104; 607/109

(58) Field of Classification Search ........... 607/104, 607/108–112, 114; 602/2; 62/259.3; 2/458
See application file for complete search history.

(56) References Cited

U.S. PATENT DOCUMENTS

| | | | |
|---|---|---|---|
| 3,504,674 A | 4/1970 | Swenson et al. | |
| 3,587,577 A | 6/1971 | Smirnov et al. | |
| 3,648,765 A | 3/1972 | Starr | |
| 3,811,777 A | 5/1974 | Chance | |
| 3,830,222 A | 8/1974 | Chance | |
| 3,871,381 A | 3/1975 | Roslonski | |
| 3,963,351 A | 6/1976 | Chance et al. | |
| 4,023,905 A | 5/1977 | Chance | |
| 4,118,946 A | 10/1978 | Tubin | |
| 4,138,743 A | 2/1979 | Elkins et al. | |
| 4,162,405 A | 7/1979 | Chance et al. | |
| 4,172,495 A | 10/1979 | Zebuhr et al. | |
| 4,191,028 A | 3/1980 | Audet et al. | |
| 4,292,973 A * | 10/1981 | Yamauchi et al. ......... 607/107 |
| 4,353,359 A * | 10/1982 | Milbauer ................ 601/166 |
| 4,378,797 A | 4/1983 | Osterholm | |

(Continued)

FOREIGN PATENT DOCUMENTS

DE  28 51 602  6/1980

(Continued)

OTHER PUBLICATIONS

The Internartional Preliminary Examination Report for PCT/US03/30984 mailed Jan. 11, 2005 (8 pages).

(Continued)

*Primary Examiner*—Linda C. Dvorak
(74) *Attorney, Agent, or Firm*—Shumaker & Sieffert

(57) ABSTRACT

In general, the disclosure presents techniques for rapidly cooling the body of a patient. A cooling garment is placed in contact with the body of the patient. Spacers within the cooling garment create a space between at least a portion of the cooling garment and the body of the patient. The cooling garment receives a coolant from a coolant supply and delivers the coolant to the body of the patient. The heat from the body of the patient may evaporate the coolant. A carrier gas, which circulates within the space between the cooling garment and the patient, carries the gaseous coolant out of the cooling garment via an exit port. The rapid cooling of the patient may slow the neurological damage to the patient.

83 Claims, 11 Drawing Sheets

U.S. PATENT DOCUMENTS

| | | |
|---|---|---|
| 4,380,240 A | 4/1983 | Jobsis et al. |
| 4,382,446 A | 5/1983 | Truelock et al. |
| 4,416,285 A | 11/1983 | Shaw et al. |
| 4,425,916 A | 1/1984 | Bowen |
| 4,441,502 A | 4/1984 | Chance |
| 4,452,250 A | 6/1984 | Chance et al. |
| 4,510,938 A | 4/1985 | Jobsis et al. |
| 4,552,149 A | 11/1985 | Tatsuki |
| 4,570,638 A | 2/1986 | Stoddart et al. |
| 4,638,436 A | 1/1987 | Badger et al. |
| 4,725,147 A | 2/1988 | Stoddart |
| 4,750,493 A | 6/1988 | Brader |
| 4,753,242 A | 6/1988 | Saggers |
| 4,765,338 A | 8/1988 | Turner et al. |
| 4,768,516 A | 9/1988 | Stoddart et al. |
| 4,817,621 A | 4/1989 | Aaslid |
| 4,817,623 A | 4/1989 | Stoddart et al. |
| 4,865,038 A | 9/1989 | Rich et al. |
| 4,869,250 A | 9/1989 | Bitterly |
| 4,904,237 A | 2/1990 | Janese |
| 4,920,963 A | 5/1990 | Brader |
| 4,964,408 A | 10/1990 | Hink et al. |
| 4,972,331 A | 11/1990 | Chance |
| 4,981,136 A | 1/1991 | Chance |
| 4,987,896 A | 1/1991 | Nakamatsu |
| 5,062,428 A | 11/1991 | Chance |
| 5,080,098 A | 1/1992 | Willett et al. |
| 5,081,991 A | 1/1992 | Chance |
| 5,090,415 A | 2/1992 | Yamashita et al. |
| 5,094,240 A | 3/1992 | Muz |
| 5,110,721 A | 5/1992 | Anaise et al. |
| 5,119,815 A | 6/1992 | Chance |
| 5,122,974 A | 6/1992 | Chance |
| 5,139,025 A | 8/1992 | Lewis et al. |
| 5,140,989 A | 8/1992 | Lewis et al. |
| 5,149,321 A | 9/1992 | Klatz et al. |
| 5,163,425 A | 11/1992 | Nambu et al. |
| 5,167,230 A | 12/1992 | Chance |
| 5,187,672 A | 2/1993 | Chance et al. |
| 5,188,108 A | 2/1993 | Secker et al. |
| 5,217,013 A | 6/1993 | Lewis et al. |
| 5,234,405 A | 8/1993 | Klatz et al. |
| 5,261,243 A | 11/1993 | Dunsmore |
| 5,261,399 A | 11/1993 | Klatz et al. |
| 5,269,758 A | 12/1993 | Taheri |
| 5,287,705 A | 2/1994 | Roehrich et al. |
| 5,349,961 A | 9/1994 | Stoddart et al. |
| 5,350,417 A * | 9/1994 | Augustine .................. 607/104 |
| 5,353,799 A | 10/1994 | Chance |
| 5,365,607 A | 11/1994 | Benevento, Jr. et al. |
| 5,383,918 A | 1/1995 | Panetta |
| 5,386,827 A | 2/1995 | Chance et al. |
| 5,395,314 A | 3/1995 | Klatz et al. |
| 5,402,778 A | 4/1995 | Chance |
| 5,408,093 A | 4/1995 | Ito et al. |
| 5,409,005 A | 4/1995 | Bissonnette et al. |
| 5,449,379 A | 9/1995 | Hadtke |
| 5,465,714 A | 11/1995 | Scheuing |
| 5,477,853 A | 12/1995 | Farkas et al. |
| 5,482,034 A | 1/1996 | Lewis et al. |
| 5,486,204 A | 1/1996 | Clifton |
| 5,531,776 A | 7/1996 | Ward et al. |
| 5,553,614 A | 9/1996 | Chance |
| 5,555,885 A | 9/1996 | Chance |
| 5,564,417 A | 10/1996 | Chance |
| 5,571,142 A | 11/1996 | Brown et al. |
| 5,584,296 A | 12/1996 | Cui et al. |
| 5,584,804 A | 12/1996 | Klatz et al. |
| 5,596,987 A | 1/1997 | Chance |
| 5,603,728 A | 2/1997 | Pachys |
| 5,658,324 A | 8/1997 | Bailey, Sr. et al. |
| 5,662,690 A | 9/1997 | Cole et al. |
| 5,664,574 A | 9/1997 | Chance |
| 5,673,701 A | 10/1997 | Chance |
| 5,683,438 A | 11/1997 | Grahn |
| 5,697,367 A | 12/1997 | Lewis et al. |
| 5,700,828 A | 12/1997 | Federowicz et al. |
| 5,713,941 A | 2/1998 | Robins et al. |
| 5,716,386 A | 2/1998 | Ward et al. |
| 5,730,730 A | 3/1998 | Darling, Jr. |
| 5,755,756 A | 5/1998 | Freedman, Jr. et al. |
| 5,779,631 A | 7/1998 | Chance |
| 5,782,755 A | 7/1998 | Chance et al. |
| 5,792,051 A | 8/1998 | Chance |
| 5,795,292 A | 8/1998 | Lewis et al. |
| 5,802,865 A | 9/1998 | Strauss |
| 5,807,263 A | 9/1998 | Chance |
| 5,820,558 A | 10/1998 | Chance |
| 5,827,222 A | 10/1998 | Klatz et al. |
| 5,837,003 A | 11/1998 | Ginsburg |
| 5,853,370 A | 12/1998 | Chance et al. |
| 5,860,292 A | 1/1999 | Augustine et al. |
| 5,871,526 A | 2/1999 | Gibbs et al. |
| 5,873,821 A | 2/1999 | Chance et al. |
| 5,899,865 A | 5/1999 | Chance |
| 5,902,235 A | 5/1999 | Lewis et al. |
| 5,913,885 A | 6/1999 | Klatz et al. |
| 5,916,242 A | 6/1999 | Schwartz |
| 5,917,190 A | 6/1999 | Yodh et al. |
| 5,954,053 A | 9/1999 | Chance et al. |
| 5,957,963 A | 9/1999 | Dobak, III |
| 5,964,092 A | 10/1999 | Tozuka et al. |
| 5,987,351 A | 11/1999 | Chance |
| 6,010,528 A | 1/2000 | Augustine et al. |
| 6,012,179 A | 1/2000 | Garrett et al. |
| 6,030,412 A | 2/2000 | Klatz et al. |
| 6,044,648 A | 4/2000 | Rode |
| 6,058,324 A | 5/2000 | Chance |
| 6,090,132 A | 7/2000 | Fox |
| 6,091,989 A | 7/2000 | Swerdlow et al. |
| 6,101,413 A | 8/2000 | Olson et al. |
| 6,110,168 A | 8/2000 | Ginsburg |
| 6,119,474 A | 9/2000 | Augustine et al. |
| 6,126,680 A | 10/2000 | Wass |
| 6,148,233 A | 11/2000 | Owen et al. |
| 6,149,624 A | 11/2000 | McShane |
| 6,149,670 A | 11/2000 | Worthen et al. |
| 6,149,673 A | 11/2000 | Ginsburg |
| 6,149,677 A | 11/2000 | Dobak, III |
| 6,156,007 A | 12/2000 | Ash |
| 6,156,057 A | 12/2000 | Fox |
| 6,183,501 B1 | 2/2001 | Latham |
| 6,188,930 B1 | 2/2001 | Carson |
| 6,209,144 B1 | 4/2001 | Carter |
| 6,248,126 B1 | 6/2001 | Lesser et al. |
| 6,269,267 B1 | 7/2001 | Bardy et al. |
| 6,277,143 B1 | 8/2001 | Klatz et al. |
| 6,283,123 B1 | 9/2001 | Van Meter et al. |
| 6,303,156 B1 | 10/2001 | Ferrigno |
| 6,321,113 B1 | 11/2001 | Parker et al. |
| 6,325,818 B1 | 12/2001 | Werneth |
| 6,354,099 B1 | 3/2002 | Bieberich |
| 6,356,785 B1 | 3/2002 | Snyder et al. |
| 6,370,428 B1 | 4/2002 | Snyder et al. |
| 6,375,673 B1 | 4/2002 | Clifton et al. |
| 6,375,674 B1 | 4/2002 | Carson |
| 6,389,828 B1 | 5/2002 | Thomas |
| 6,402,775 B1 | 6/2002 | Bieberich |
| 6,406,427 B1 | 6/2002 | Williams et al. |
| 6,409,745 B1 * | 6/2002 | Ducharme et al. .......... 607/108 |
| 6,416,480 B1 | 7/2002 | Nenov |
| 6,426,759 B1 | 7/2002 | Ting et al. |
| 6,432,124 B1 | 8/2002 | Worthen et al. |
| 6,451,045 B1 | 9/2002 | Walker et al. |

| | | |
|---|---|---|
| 6,461,379 B1 * | 10/2002 | Carson et al. ............... 607/104 |
| 6,473,920 B2 * | 11/2002 | Augustine et al. ............. 5/423 |
| 6,487,871 B1 | 12/2002 | Augustine et al. |
| 6,497,358 B1 | 12/2002 | Walsh |
| 6,497,720 B1 | 12/2002 | Augustine et al. |
| 6,497,721 B2 | 12/2002 | Ginsburg et al. |
| 6,508,831 B1 | 1/2003 | Kushnir |
| 6,511,502 B2 | 1/2003 | Fletcher |
| 6,516,224 B2 | 2/2003 | Lasersohn et al. |
| 6,519,964 B2 | 2/2003 | Bieberich |
| 6,520,933 B1 | 2/2003 | Evans et al. |
| 6,523,354 B1 | 2/2003 | Tolbert |
| 6,527,798 B2 | 3/2003 | Ginsburg et al. |
| 6,544,282 B1 | 4/2003 | Dae et al. |
| 6,547,811 B1 | 4/2003 | Becker et al. |
| 6,551,347 B1 | 4/2003 | Elkins |
| 6,551,348 B1 | 4/2003 | Blalock et al. |
| 6,551,349 B2 | 4/2003 | Lasheras et al. |
| 6,558,412 B2 | 5/2003 | Dobak, III |
| 6,558,413 B2 | 5/2003 | Augustine et al. |
| 6,576,002 B2 | 6/2003 | Dobak, III |
| 6,581,400 B2 * | 6/2003 | Augustine et al. ......... 62/259.3 |
| 6,582,398 B1 | 6/2003 | Worthen et al. |
| 6,582,455 B1 | 6/2003 | Dobak, III et al. |
| 6,599,312 B2 | 7/2003 | Dobak, III |
| 6,607,517 B1 | 8/2003 | Dae et al. |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,516 B2 | 9/2003 | Saab |
| 6,635,076 B1 | 10/2003 | Ginsburg |
| 6,645,232 B2 | 11/2003 | Carson |
| 6,645,234 B2 | 11/2003 | Evans et al. |
| 6,656,208 B2 | 12/2003 | Grahn et al. |
| 6,656,209 B1 | 12/2003 | Ginsburg |
| 6,682,550 B2 * | 1/2004 | Clifton et al. ............... 607/104 |
| 6,692,518 B2 | 2/2004 | Carson |
| 6,697,671 B1 | 2/2004 | Nova et al. |
| 6,800,087 B2 | 10/2004 | Papay et al. |
| 6,813,517 B2 | 11/2004 | Daynes et al. |
| 6,829,501 B2 | 12/2004 | Nielsen et al. |
| 6,887,199 B2 | 5/2005 | Bridger et al. |
| 2001/0021866 A1 | 9/2001 | Dobak, III et al. |
| 2001/0027333 A1 | 10/2001 | Schwartz |
| 2001/0027334 A1 | 10/2001 | White |
| 2001/0039439 A1 | 11/2001 | Elkins et al. |
| 2001/0049545 A1 | 12/2001 | Lasersohn et al. |
| 2001/0051801 A1 | 12/2001 | Lehmann et al. |
| 2002/0002394 A1 | 1/2002 | Dobak, III |
| 2002/0004729 A1 | 1/2002 | Zak et al. |
| 2002/0007201 A1 | 1/2002 | Grahn et al. |
| 2002/0026226 A1 | 2/2002 | Ein |
| 2002/0029073 A1 | 3/2002 | Schwartz |
| 2002/0032473 A1 | 3/2002 | Kushnir et al. |
| 2002/0072785 A1 | 6/2002 | Nelson et al. |
| 2002/0091428 A1 | 7/2002 | Larnard et al. |
| 2002/0091431 A1 | 7/2002 | Gunn et al. |
| 2002/0095200 A1 | 7/2002 | Dobak, III et al. |
| 2002/0095201 A1 | 7/2002 | Worthen et al. |
| 2002/0099427 A1 | 7/2002 | Dobak, III |
| 2002/0103508 A1 | 8/2002 | Mathur |
| 2002/0103520 A1 | 8/2002 | Latham |
| 2002/0116041 A1 | 8/2002 | Daoud |
| 2002/0120317 A1 | 8/2002 | Fletcher |
| 2002/0138302 A1 | 9/2002 | Bodnick |
| 2002/0151946 A1 | 10/2002 | Dobak, III |
| 2002/0183815 A1 | 12/2002 | Nest et al. |
| 2002/0183816 A1 | 12/2002 | Tzeng et al. |
| 2002/0193852 A1 | 12/2002 | Renfro |
| 2002/0193853 A1 | 12/2002 | Worthen et al. |
| 2002/0193854 A1 | 12/2002 | Dobak, III et al. |
| 2002/0193855 A1 | 12/2002 | Dobak, III |
| 2002/0198578 A1 | 12/2002 | Dobak, III |
| 2003/0018375 A1 | 1/2003 | Dobak, III et al. |
| 2003/0023288 A1 | 1/2003 | Magers |
| 2003/0036786 A1 | 2/2003 | Duren et al. |
| 2003/0040782 A1 | 2/2003 | Walker et al. |
| 2003/0040783 A1 | 2/2003 | Salmon |
| 2003/0055472 A1 | 3/2003 | Worthen |
| 2003/0055473 A1 | 3/2003 | Ramsden et al. |
| 2003/0060863 A1 | 3/2003 | Dobak, III |
| 2003/0060864 A1 | 3/2003 | Whitebrook et al. |
| 2003/0066304 A1 | 4/2003 | Becker et al. |
| 2003/0078638 A1 | 4/2003 | Voorhees et al. |
| 2003/0078639 A1 | 4/2003 | Carson |
| 2003/0078640 A1 | 4/2003 | Carson et al. |
| 2003/0083721 A1 | 5/2003 | Larnard |
| 2003/0088299 A1 | 5/2003 | Magers et al. |
| 2003/0088300 A1 | 5/2003 | Vester |
| 2003/0114903 A1 | 6/2003 | Ellingboe |
| 2003/0135252 A1 | 7/2003 | MacHold et al. |
| 2003/0144714 A1 | 7/2003 | Dobak, III |
| 2003/0150545 A1 | 8/2003 | Szczesuil et al. |
| 2003/0195597 A1 | 10/2003 | Keller et al. |
| 2003/0216799 A1 | 11/2003 | Worthen et al. |
| 2003/0225336 A1 | 12/2003 | Callister et al. |
| 2004/0158303 A1 | 8/2004 | Lennox et al. |

FOREIGN PATENT DOCUMENTS

| | | |
|---|---|---|
| GB | 764993 | 1/1957 |
| JP | 8084744 | 4/1996 |
| JP | 9182766 | 7/1997 |
| JP | 9220251 | 8/1997 |
| JP | 10258080 | 9/1998 |
| JP | 10277080 | 10/1998 |
| WO | WO 99/08632 | 2/1999 |
| WO | WO 99/23980 A1 | 5/1999 |
| WO | WO 99/23989 A1 | 5/1999 |
| WO | WO 99/44552 A1 | 9/1999 |
| WO | WO 00/33236 A1 | 6/2000 |
| WO | WO 01/95977 A1 | 12/2001 |
| WO | WO 02/41231 A2 | 5/2002 |

OTHER PUBLICATIONS

Sophie Cluet and Claude Delobel, "A General Framework for the Optimization of Object-Oriented Queries," ACM SIGMOD Record vol. 21, Issue 2, pp. 383-392 (Jun. 1992).

US 6,645,236, 11/2003, Lachenbruch et al. (withdrawn)

* cited by examiner

RAPID INDUCTION OF MILD HYPOTHERMIA

TECHNICAL FIELD

The invention relates to medical devices that control the temperature of a patient, and more particularly, to medical devices that cool one or more parts of the body of a patient.

BACKGROUND

Some medical conditions may be treated by hypothermia. In many cases, hypothermic therapy within the first few minutes of the onset of a condition may mean the difference between life and death. In some cases in which the patient is spared death, prompt hypothermic therapy may make a dramatic difference in the quality of life of the patient.

Stroke is an example of a medical condition that may be treated by prompt administration of hypothermic therapy. Many patients that suffer strokes die as a result of the stroke, and a significant fraction of those who survive suffer some degree of neurological damage. The neurological damage to the patient may be slowed by the application of hypothermic therapy.

There have been many different techniques studied to produce hypothermia in the body, including invasive and non-invasive techniques, such as the use of cold packs, ice blankets, injecting a cooled saline solution into the blood stream, heating the hypothalamus, cooling the air around the patient, and circulating of a coolant fluid around the patient. Some techniques are more effective than others. Many of these techniques involve bulky apparatuses that are difficult to transport to the patient, and are usually available only in a hospital setting. In addition, many of these techniques rely upon the training of specially skilled hospital personnel. There may be a significant delay in administration of hypothermic therapy while the patient is being taken to the hospital.

SUMMARY

In general, the invention provides techniques for cooling a patient to provide hypothermic therapy. In particular, a cooling garment is placed in contact with the body of a patient. The cooling garment may include one or more garments in contact with the body of a patient. For example, the cooling garment may include a headgear in contact with the head of the patient, an upper body gear in contact with the upper torso or armpit of the patient, and a lower body gear in contact with the legs or groin of the patient. Spacers within the cooling garment may separate at least a portion of the cooling garment from the body of the patient creating a space. The cooling garment receives a liquid coolant from a coolant supply and a carrier gas from a carrier gas supply. The carrier gas may also be a coolant gas. The cooling garment may apply the liquid coolant directly to the skin of the patient. Alternatively, the cooling garment may apply the liquid coolant to an absorbent layer in contact with the skin of the patient. The carrier gas circulates within the space created by the spacers. Heat from the body of the patient and gas flow may cause the liquid coolant to change from a liquid phase to a gaseous phase, i.e., to evaporate. The carrier gas carries the gaseous coolant out of the cooling device via an exit port.

In one embodiment, the invention is directed to a device that comprises a garment for placing in contact with a body part of a patient. The device further includes a spacer for separating at least part of the garment from the body defining a space. The device further comprises a coolant delivery conduit for delivering a coolant to the body in the space. The device includes a carrier gas intake port in the garment for fluidly connecting the space to a carrier gas supply. The device also includes an exit port in the garment for fluidly connecting the space to an exterior environment.

In another embodiment, the invention is directed to a system that includes a headgear for contacting at least a portion of a head of a patient and a body gear for contacting at least a portion of a body part of the patient other than the head. The system further comprises a coolant supply container for supplying coolant to both the headgear and the body gear.

In another embodiment, the invention presents a method that comprises separating at least a portion of a cooling garment from a body part of a patient to create a space. The method further comprises allowing a coolant to exit a coolant delivery conduit onto the body in the space. The method includes allowing a carrier gas to enter the space via a carrier gas port. The method also includes expelling the coolant in a gaseous state from an exit port in the garment.

In another embodiment, the invention is directed to a device comprising an inner shell proximate to a body part of a patient, a space between the body part and the inner shell being an inner space. The device further comprises an outer shell surrounding the inner shell, a space between the outer shell and the inner shell being an outer space in fluid communication with the inner space. The device also includes an exit port for expelling a coolant and a gas, the gas moving from the outer space to the inner space.

The invention may provide one or more advantages. For example, the use of rapid hypothermic therapy may prevent the patient from suffering permanent brain damage. Emergency medical personnel, who are often the first to reach the patient, can administer the techniques. The cooling garment may allow for hands free operation. For example, once on the body of the patient, the user may administer other treatments. In addition, the cooling garment may be constructed to be light and portable in some embodiments, and may be brought to the patient at the site of the traumatic event, or at least contained in an ambulance. Further, the cooling garment or parts of the cooling garment may be sterilizable and, therefore, reusable. The cooling garment may also be powered by any source, including alternating current (AC) and direct current (DC).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
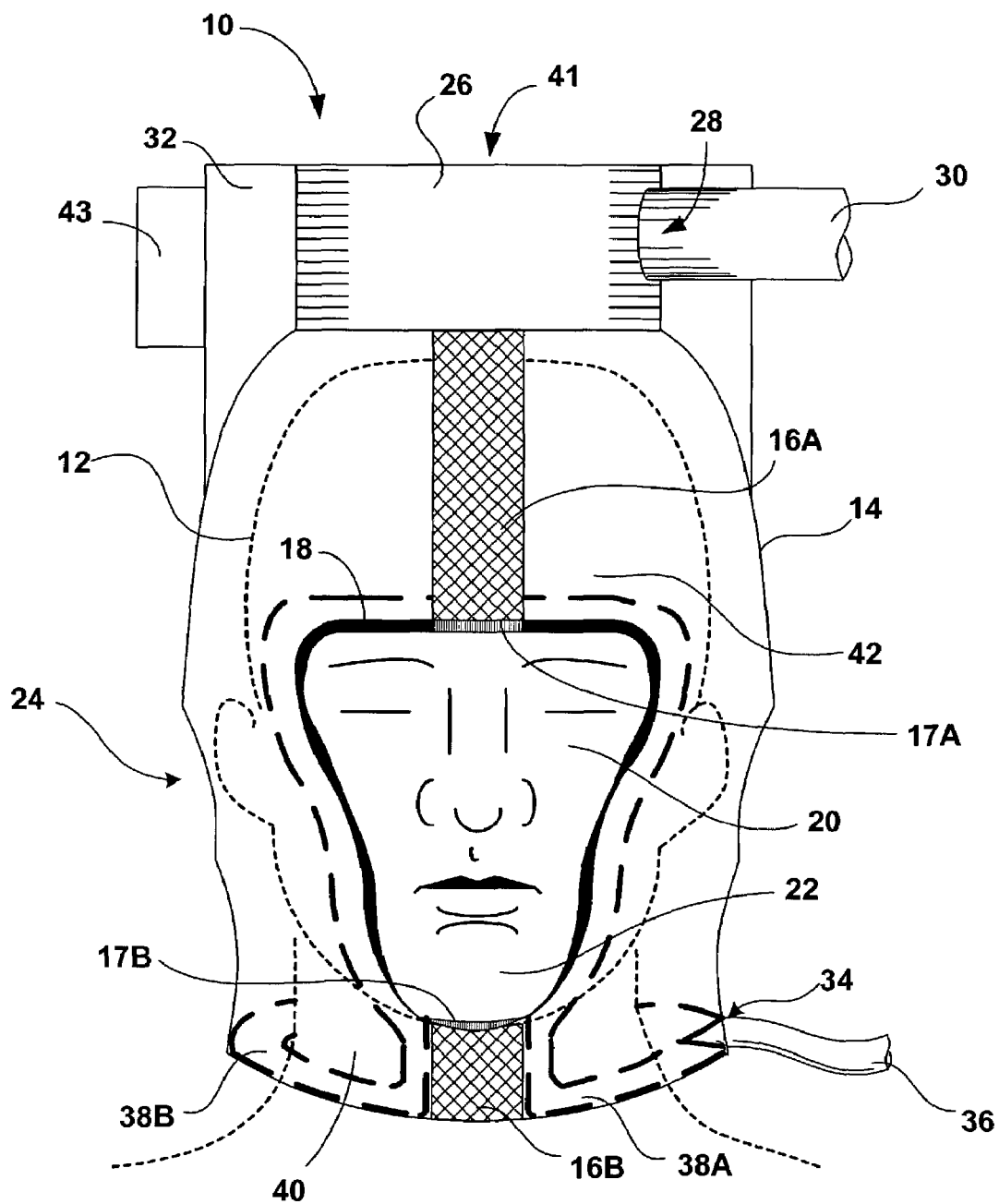
FIG. 1 is a schematic diagram illustrating a front view of an exemplary headgear used for cooling of a patient, according to an embodiment of the invention.

FIG. 1 is a schematic front view of an exemplary headgear 10 used for cooling of a patient 12. Headgear 10 is one embodiment of a cooling garment. Headgear 10 comprises a deformable enclosure member 14. Enclosure member 14 deforms so that enclosure member 14 may be placed upon the head of patient 12. Enclosure member 14 includes one or more spacers (not shown) that separate at least a portion of enclosure member 14 from the body of patient 12 defining a space. A spacer may be coupled to headgear 10. Alternatively, a spacer may detach from headgear 10.

Once placed upon the head of patient 12, enclosure member 14 may be held in place with fasteners 16A and 16B (collectively fasteners 16), allowing a user, such as emergency medical personnel to administer other treatments to patient 12. Fastener 16A adjusts just above face 20 and fastener 16B adjusts under chin 22, so as to fit around different size heads. Securing fasteners 16 causes seal members 17A and 17B (collectively seal members 17) to contact the body of patient 12, substantially isolating the space inside enclosure member 14 from an exterior environment.

Enclosure member 14 may be formed from a substantially compliant material, such as rubber, plastic, or airtight cloth. Enclosure member 14 may have a different rigidity for an anterior portion as opposed to a posterior portion. For example, the posterior of enclosure member 14 may be more rigid in order to support the weight of patient 12. Seal members 17 may be formed from a pliable material such as rubber, plastic, or silicone, and may be sewn, bonded, or otherwise affixed to enclosure member 14. Seal member 17, for example, may be a flexible rubber web, an O-ring tube seal, a collapsible tube or the like. Fasteners 16 may be any sort of fastening device such as a zipper, a hook and loon fastener such as VELCRO, a button, a clip, a buckle, a strap, an adhesive, or the like.

Enclosure member 14 may include an ear access 24, which allows outside access to the ear of patient 12 when headgear 10 is in place on the head. The temperature of patient 12 may be measured through ear access 24. Ear access 24 may be embodied as an aperture in enclosure member 14, an earflap, or the like. Enclosure member 14 may further include other body accesses that allow access to other portions of the head.

Headgear 10 further comprises a gas intake/outflow unit 26. Gas intake/outflow unit 26 may include a carrier gas intake port 28 that receives a carrier gas supply 30. Gas intake/outflow unit 26 may be substantially rigid, and may be formed from materials such as non-corrosive metal, plastic, or rubber. Gas intake/outflow unit 26 and, more particularly, carrier gas intake port 28, fluidly connects the space between the head of patient 12 and enclosure member 14 to carrier gas supply 30. In general, gas intake/outflow unit 26 receives a carrier gas from carrier gas supply 30. A carrier gas mover (not shown) moves the carrier gas within the space. The operation of gas intake/outflow unit 26 will be described in more detail below. The carrier gas may be carbon dioxide, nitrogen, air or the like. Alternatively, the carrier gas may be a mixture of gases. For example, the carrier gas may be a mixture of carbon dioxide and air. In one instance, air may be mixed with the carbon dioxide to reduce the temperature of the carrier gas for the safety of the patient. Carrier gases such as carbon dioxide and nitrogen may be more effective than air in absorbing evaporated coolant, especially in an environment with high humidity. For reasons of safety, the carrier gas may be a gas other than oxygen and non-reactive with oxygen.

Headgear 10 may further include a coolant port 34 that receives a coolant supply 36. Coolant port 34 brings coolant supply 36 into fluid communication with a coolant delivery conduit 38. Coolant delivery conduit 38 may branch at coolant port 34 into coolant delivery conduit branch 38A and 38B. Coolant delivery conduit branch 38A may carry a liquid coolant into headgear 10, anteriorly to approximately under chin 22, around left side of face 20 of patient 12, and to the edge of fastener 16A. Coolant delivery conduit branch 38B may carry the liquid coolant posteriorly around neck 40 of patient 12, then anteriorly to approximately under chin 22, around right side of face 20, and to the edge of fastener 16A. In particular, coolant delivery conduit 38 may extend from coolant port 34 posteriorly around neck 40 to approximately under chin 22 in both directions. Coolant delivery conduit 38 may proceed from chin 22 around face 20 and terminate at two sites proximate to fastener 16A. The invention encompasses coolant delivery conduit 38 branching in a fashion different than described above, or not branching at all.

The pressure of the coolant in coolant delivery conduit 38 may form a seal member 18 for the portions of headgear 10 around neck 40 and face 20. In other words, coolant delivery conduit 38 may transport coolant around the head and form a seal proximate to face 20. Seal members 17 create the seal at sites around face 20 where coolant delivery conduit 38 does not extend. Alternatively, coolant delivery conduit 38 may not be a seal member, in which case seal members 17 may create the seal around face 20. Coolant delivery conduit 38 and/or seal members 17 may also be a spacer that creates the space between the patient and headgear 10.

Coolant delivery conduit 38 may be flexibly formed from tube-like structures made of materials such as rubber, plastic, or the like. Coolant delivery conduit 38 may be shaped to expand and contract to accommodate heads of different sizes and shapes. Examples of construction of coolant delivery conduit 38 will be described in more detail below.

Coolant supply 36 is a tube-like structure, which may allow one-way or two-way flow of the coolant. Coolant supply 36 may be constructed of flexible tube-like structures made of materials such as rubber, plastic, silicone or the like. Coolant supply 36 may include a quick-connect coupling (not shown) that mates to coolant port 34. In a typical application, coolant supply 36 may be coupled to coolant port 34 after headgear 10 is placed upon the head of patient 12.

Coolant delivery conduit 38 may include small apertures (not shown) that allow the coolant to drip out, seep out, mist out, spray out, or otherwise exit the lumen of coolant delivery conduit 38. In the example of FIG. 1, the coolant that exits from coolant delivery conduit 38 may be applied to the body of patient 12. For example, the coolant that exits coolant delivery conduit 38 may be applied to an absorbent layer in contact with the body. The absorbent layer absorbs the coolant and keeps the coolant in contact with the body. The absorbent layer may further prevent the coolant from pooling up in areas where gravity tends to pull the coolant. The absorbent layer may be constructed of material such as polypropylene, cotton, or the like. The coolant may also be applied directly to the body of patient 12. Although in this embodiment the liquid coolant is applied to the body of patient 12, the invention may further include applying the liquid coolant inside the headgear in other fashions. For example, the coolant that exits from coolant delivery conduit 38 may also mix with the carrier gas from carrier gas supply 30. Liquid coolant need not come in direct contact with the body of patient 12.

The coolant is typically a liquid that evaporates due to the heat generated by the head of patient 12 or by a gas flowing over the coolant. Alcohol, water, or a mixture of alcohol and water are examples of typical coolants. However, the coolant may also be a gas or a gel. Liquid coolants accept heat and undergoes a state change to gaseous form. This heat of transformation can be substantial. The state change of the coolant inside of headgear 10 draws body heat and thereby cools patient 12. Coolant applied to the body of patient 12 may draw body heat from direct contact of the coolant and patient 12 through this evaporation process. If the coolant that is applied within headgear 10 is not applied directly to the body, such as the example of mixing coolant with a carrier gas, the coolant may draw body heat from direct contact of the coolant and patient 12 or from heat propagating outward from patient 12 by radiation or convection. Carrier gas and coolant in gaseous form are discharged through an exit port 41 located within gas intake/outflow unit 26 as will be described below, and fresh carrier gas and coolant replace what has been discharged.

Headgear 10 may include multiple coolant delivery conduits, multiple gas intake ports or both. Multiple conduits and intake ports may allow for localized cooling of portions of the head. For example, headgear 10 may include four cooling areas. Each cooling area may be served by a discrete coolant delivery conduit 38 and a gas intake port 28. Alternatively, each cooling area may include a common coolant delivery conduit 38 and separate gas intake port 28. The cooling areas may be separated from one another by one or more dividers that isolate the space of one cooling area from the space of neighboring cooling areas. The same coolant supply 36 may supply coolant to each of the coolant delivery conduits. Alternatively, a separate coolant supply 36 may supply coolant to each of the coolant delivery conduits. Carrier gas intake ports 28 may also be supplied by the same carrier gas supply or multiple carrier gas supplies.

As will be described below, a housing 32 may house a processor to process information that the processor receives from optical fiber links, a wireless link, wire link, and the like. For example, the processor may receive information in the form of signals from one or more sensors on the body of patient 12. Headgear 10 may further comprise a battery pack 43 that operates headgear 10 when no AC power source is available. For example, battery pack 43 may power the processor at the location of a traumatic event. Battery pack 43 may also power the carrier gas mover or any other electric or electronic components of headgear 10. In this manner, headgear 10 may be powered by any source, including an alternating current (AC) power source and a direct current (DC) power source.

Figure 2:
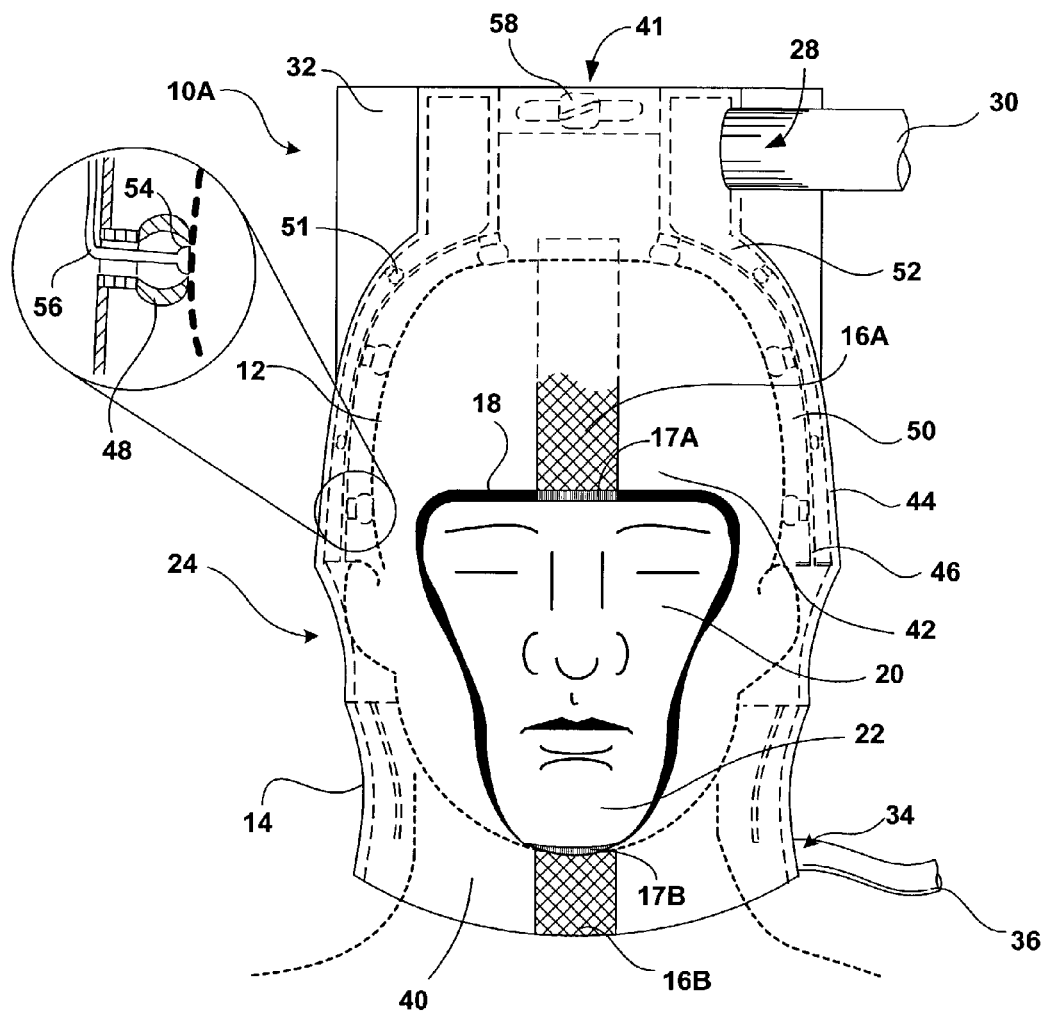
FIG. 2 is a schematic diagram illustrating a front view of an embodiment the headgear shown in FIG. 1.

FIG. 2 is a schematic front view of an embodiment of headgear 10 of FIG. 1. Headgear 10A may further comprise an outer shell 44 and an inner shell 46. A set of inner spacers 48 creates a separation between patient 12 and inner shell 46, the separation between patient 12 and inner shell 46 referred to hereinafter as an inner space 50. A set of outer spacers 51 creates a separation between outer shell 44 and inner shell 46, the separation outer shell 44 and inner shell 46 referred to hereinafter as an outer space 52. Inner space 50 is in fluid communication with outer space 52. Inner shell 46 may be constructed from a rigid to semi-rigid material such as a plastic, rubber or the like. Outer shell 44 may be constructed from a rigid to semi-rigid material that is also electrically insulated such as plastic, rubber, or the like. Outer shell 44 may be constructed from a rigid to semi-rigid material that is also electrically insulated. Insulation of outer shell 44 may prevent interference with electrical equipment concurrently being used for treatment and monitoring of patient 12. Inner spacers 48 and outer spacers 51 may be constructed from materials such as plastic, rubber, or the like. Alternatively, spacers 48 and 50 may be a chain, air, or the like.

Inner spacers 48 may house within them at least one sensor 54 and a communication link 56. Sensor 54 generates a signal as a function of a patient parameter such as temperature, oxygen saturation levels, blood flow, heart rate, brain electrical action, end tidal carbon dioxide levels or the like. Communication link 56 then relays the signal to a processor, which may be housed in housing 32. Sensor 54 may be an assortment of sensor devices such as a temperature sensor, a thermocouple, an oxygen sensor, a velocity Doppler probe, an electrocardiogram (ECG) sensor, an electroencephalograph (EEG) sensor, or the like. Communication link 56 may include an optical fiber link, a wireless link, a wire link, or the like.

Carrier gas entering headgear 10A at carrier gas port 28 enters outer space 52 in gas intake/outflow unit 26. Carrier gas flows in outer space 52 from the crown of the head toward the neck, where carrier gas enters inner space 50. Carrier gas flows in inner space 50 from the neck to the crown, exiting at exit port 41 in gas intake/outflow unit 26. Gas intake/outflow unit 26 may include a carrier gas mover, such as a fan 58, that circulates carrier gas within headgear 10A. Other carrier gas movers, such as a pressurized carrier gas supply or a pump, may be used to move the carrier gas instead of or in addition to fan 58.

Figure 3:
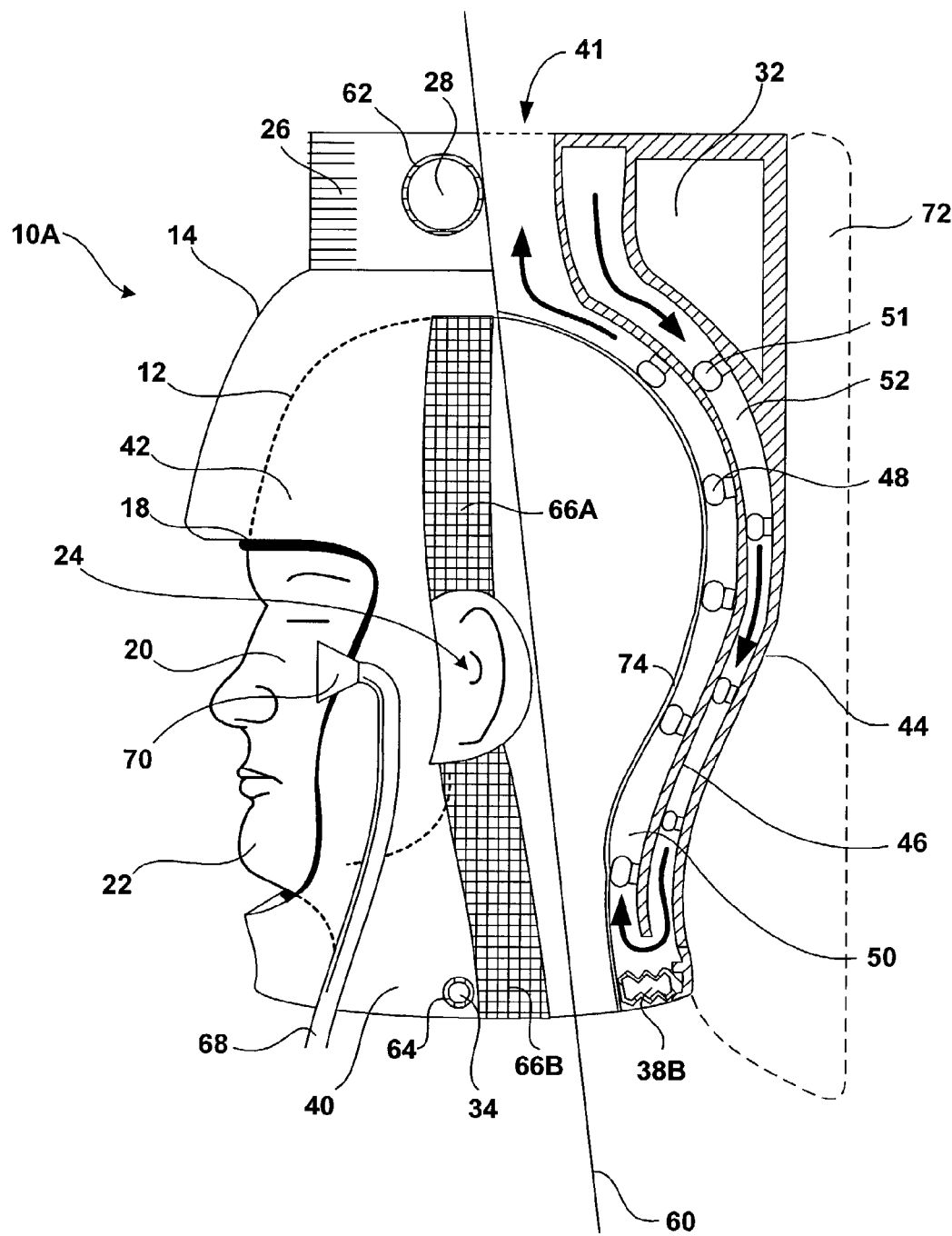
FIG. 3 is a schematic diagram illustrating a split cross-sectional profile of the exemplary headgear of FIG. 2.

FIG. 3 is a schematic diagram illustrating a split cross-sectional profile of exemplary headgear 10A of FIG. 2. The outer profile of headgear 10A is shown to the left of line 60 and the inner cross-sectional profile of headgear 10A is shown to the right of line 60.

Headgear 10A may comprise a gas fitting 62 mated to carrier gas port 28. Gas fitting 62 may be a quick-connect coupling that mates carrier gas supply 30 to gas intake/outflow unit 26. Headgear 10A may further comprise a coolant fitting 64. Coolant fitting 64 may be a quick-connect coupling that mates coolant supply 36 to coolant port 34.

Headgear 10A may also comprise expanders 66A and 66B (collectively expanders 66). Expanders 66 allow headgear 10A to expand to accommodate different sizes and shapes of heads. As mentioned previously, the material of headgear 10A may be more rigid posteriorly from expanders 66 to the back of the head of patient 12 than anteriorly from expanders 66 to the face 20 of patient 12. Expanders 66 may be constructed from a material with the ability to stretch and contract, such as spandex, rubber, elastic or the like.

Headgear 10A may further comprise a warm air supply 68 and a warm air nozzle 70 to blow warm air on face 20 of patient 12. When patient 12 undergoes cooling, patient 12 may shiver. Shivering generates heat and is counterproductive to the cooling process. Warm air applied via warm air nozzle 70 to face 20 may reduce shivering. In addition, warm air supply 68 and warm air nozzle 70 may be applied with enough pressure to blow coolant and carrier gas that may leak from headgear 10A away from the eyes, nose, or mouth of patient 12. Warm air supply 68 may be made of a tube-like structure made of materials such as rubber, plastic, or the like. Warm air nozzle 70 receives warm air from warm air supply 68, and may spread the warm air to cover a substantial portion of face 20.

Headgear 10A may also comprise a support pad 72 to support the head of patient 12. Since patient 12 will be lying for most of the monitoring and treatment procedures, support pad 72 will give patient 12 some level of comfort. Furthermore, support pad 72 may prevent wear to the backside of headgear 10A from friction between the ground and headgear 10A. Support pad 72 may be any type of padding such as a pillow, a cushion, and the like. Support pad 72 of FIG. 3 is shown as an extension from outer shell 44. Alternatively, support pad 72 may be located within headgear 10A, and may further be absorbent to collect excess coolant to prevent the coolant from pooling up in areas where gravity tends to pull the coolant, such as the back of the head and neck.

The inner profile of headgear 10A, shown to the right of line 60, illustrates how headgear 10A circulates carrier gas. Carrier gas supply 30 is coupled to gas port 28 via gas fitting 62. The carrier gas from carrier gas supply 30 enters outer space 52 in gas intake/outflow unit 26.

Coolant supply 36 is coupled to coolant port 34 via cooling fitting 64. The coolant from coolant supply 36 enters headgear 10A and is carried by coolant delivery conduit 38. Coolant delivery conduit 38 branches proximate to coolant port 34, and coolant delivery conduit branch 38B carries coolant posteriorly around the neck.

A cross-section of coolant delivery conduit branch 38B is shown in FIG. 3. In the embodiment shown in FIG. 3, coolant delivery conduit 38 has a pleated cross-section that allows coolant delivery conduit 38 to conform to different sizes of necks.

Small apertures in coolant delivery conduit 38 may allow the coolant to drip out, mist out, seep out, spray out, or otherwise exit the lumen of cooling conduit 38 throughout the entire path of cooling conduit 38. In the example of FIG. 3, the coolant exits the lumen of cooling conduit 38 via small apertures and is applied to an absorbent layer 74 that is in contact with the head of patient 12. For example, the coolant may exit cooling conduit 38 around the face 20, and the coolant may migrate within the absorbent layer down the sides of the head. The absorbent material absorbs the coolant preventing the coolant from pooling in areas of the body, such as the back of the head. Although this embodiment applies the coolant from coolant delivery conduit 38 directly to the body of patient 12, the invention encompasses variants of applying coolant within headgear 10A such as carrying the coolant exiting the lumen of coolant delivery conduit 38 with a carrier gas.

Circulation created by a carrier gas mover, such as fan 58, may cause the carrier gas to flow from crown toward neck in outer space 52, and enter inner space 50 proximate to the neck. The coolant accepts heat from direct contact with patient 12 and evaporates. The evaporation and associated convection cools patient 12. Carrier gas and coolant in gaseous form are discharged through exit port 41 of gas intake/outflow unit 26.

Figure 4:
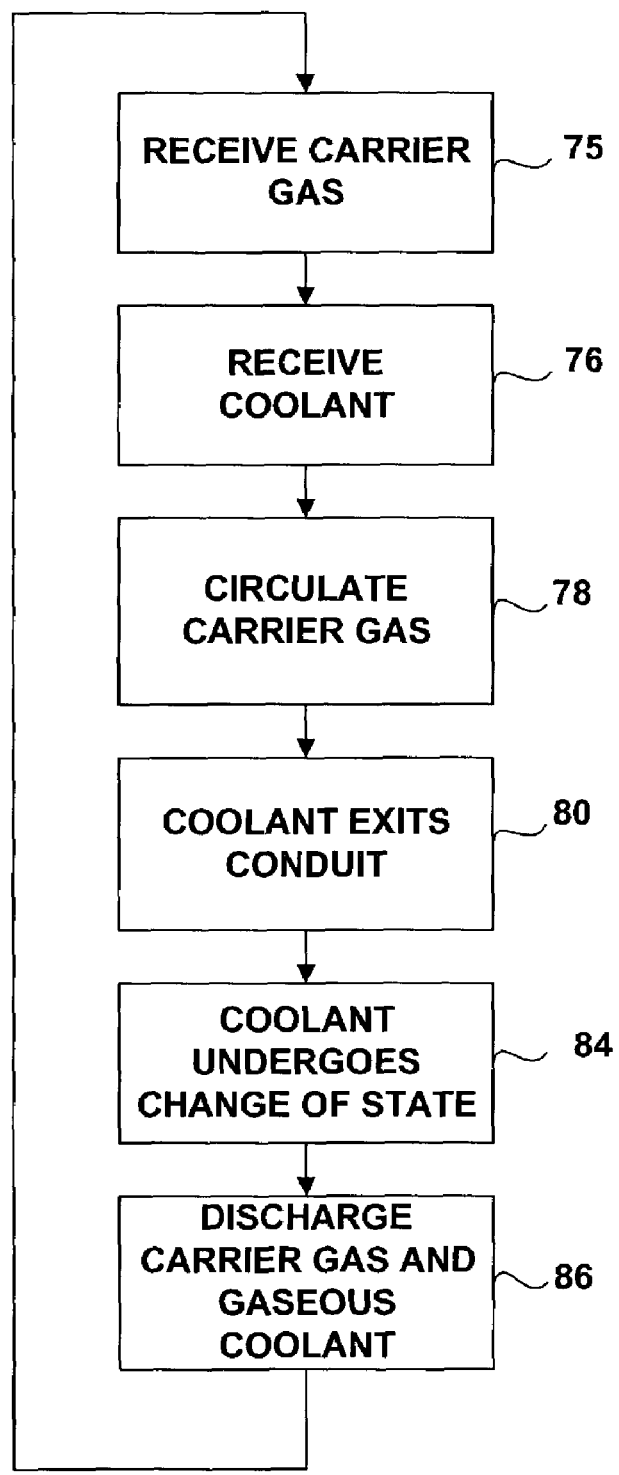
FIG. 4 is a flow diagram illustrating the cooling process occurring inside the headgear of FIG. 2.

FIG. 4 is a flow diagram illustrating the cooling process occurring inside headgear 10A. Headgear 10A and, more particularly, outer space 52 receives a carrier gas from carrier gas supply 30 (75). The incoming carrier gas may be dehumidified to enhance the evaporative cooling process. Further, the incoming carrier gas may be cooled using a carrier gas cooler such as a blue ice canister or a heat exchanger in order to enhance the evaporative cooling process.

Coolant delivery conduit 38 of headgear 10A further receives a coolant from coolant supply 36 via coolant port 64 (76). The coolant may be any kind of liquid such as water, alcohol, or a mixture of the two. Alcohol or an alcohol-water mixture may be a more effective coolant than water because alcohol evaporates more readily than water and can vaporize at cooler temperatures.

A carrier gas mover circulates the carrier gas inside headgear 10A. In FIGS. 2 and 3, for example, fan 58 or the carrier gas pressure moves the carrier gas through outer space 52 and inner space 50 (78). The carrier gas mover may increase the speed of circulation of the carrier gas to enhance the effectiveness of the evaporation process. Further, the size of inner space 50 and outer space 52 may further affect the effectiveness of the evaporation process. For example, an increase in gap size increases the effectiveness of the evaporation process.

Coolant conduit 38 allows the liquid coolant to escape from the lumen of coolant conduit 38 via small apertures (80). The liquid coolant may exit the lumen of coolant delivery conduit 38 throughout the entire path of coolant delivery conduit 38. Alternatively, the liquid coolant may exit the lumen of coolant delivery conduit 38 throughout portions of the path of coolant delivery conduit 38. Liquid coolant may exit the lumen of coolant delivery conduit 38 by, for example, dripping out, spraying out, seeping out, or misting out.

Coolant delivery conduit 38 brings the coolant into contact with the body of patient 12. The coolant may contact the body in absorbent layer 74 or may be applied directly to the body of patient 12. Heat from the body causes the coolant to undergo a state change (84), i.e., to evaporate. The evaporation and associated convection cools patient 12. The associated convection may dominate the cooling in the early stages of the process, whereas the evaporation may dominate the cooling in later stages of the cooling process as the body temperature of patient 12 begins to become closer to the temperature of the carrier gas.

In FIGS. 2 and 3, the circulating carrier gas encounters evaporated coolant principally in inner space 50. The circulating carrier gas carries the coolant in gaseous form away from patient 12. In FIGS. 2 and 3, the carrier gas carries the evaporated coolant in inner space 50 toward the crown. The carrier gas and gaseous coolant are discharged through out exit port 41 of gas intake/outflow unit 26 (86). Fresh carrier gas and coolant replace what has been discharged.

Figure 5:
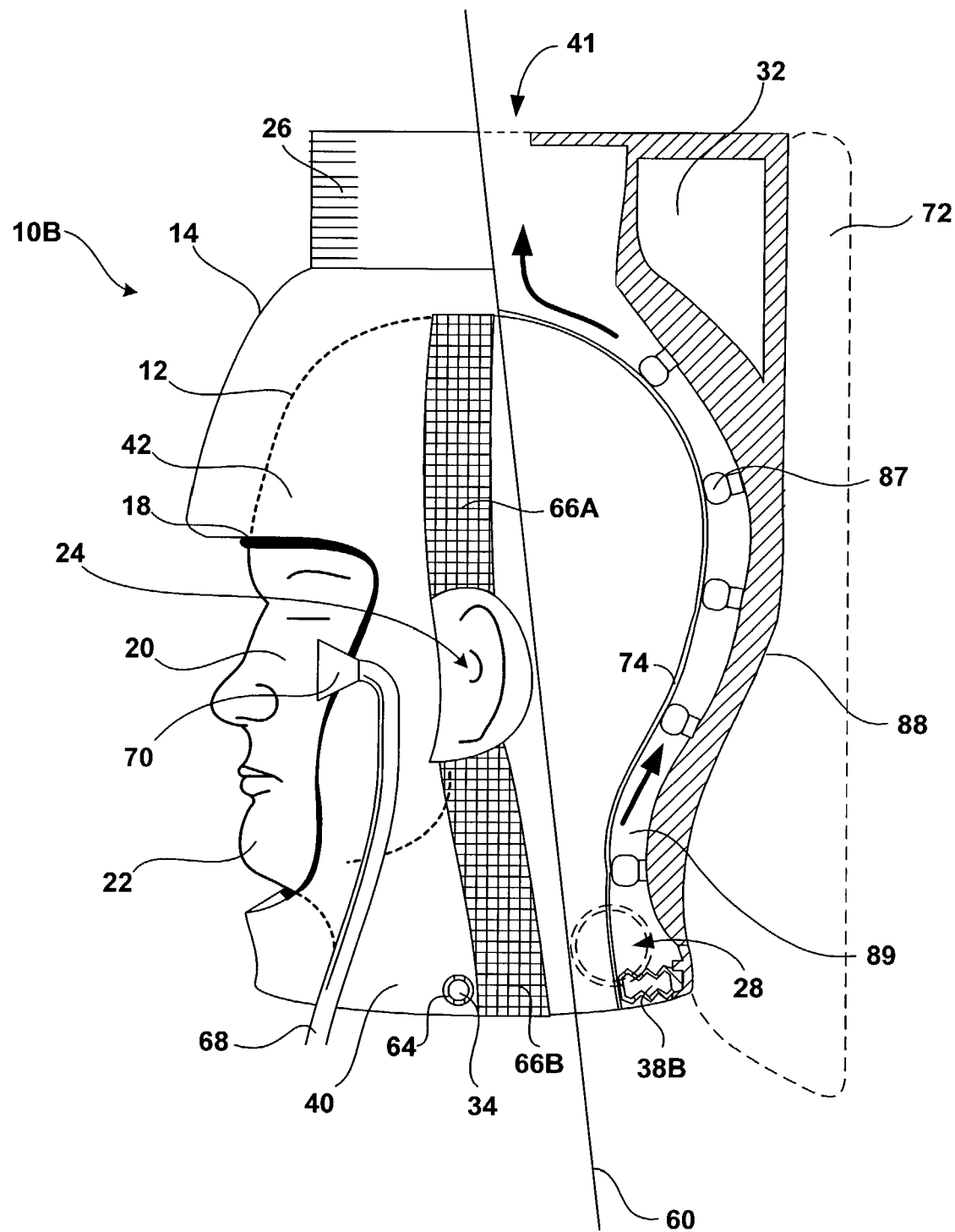
FIG. 5 is a schematic diagram illustrating a cross-sectional view of another embodiment of the headgear of FIG. 1.

FIG. 5 is a schematic diagram illustrating a cross-sectional view of another embodiment of headgear 10 of FIG. 1. Headgear 10B is similar to headgear 10 of FIG. 1, but carrier gas intake 28 of headgear 10B receives a carrier gas near the bottom portion proximate to the neck of patient 12. Carrier gas intake 28 may be proximate to coolant port 34, for example. Headgear 10B may further comprise a shell 88. A set of spacers 87 creates a separation between patient 12 and shell 88, the separation between patient 12 and shell 88 referred to hereinafter as head space 89. Shell 88 may be constructed from a rigid material that is also electrically insulated such as a rigid plastic, rubber or the like. Spacers 87 may be constructed from materials such as plastic, rubber, or the like. Alternatively, spacers 87 may be a chain, air, or the like.

Spacers 87 may house within them at least one sensor and a communication link (neither shown in FIG. 5), similar to spacers 54 of headgear 10A. The sensor generates a signal as a function of a patient parameter such as temperature, oxygen saturation levels, blood flow, heart rate, brain electrical action, end tidal carbon dioxide levels or the like. The communication link then relays the signal to a processor, which may be housed in housing 32. The sensor may be an assortment of sensor devices such as a temperature sensor, a thermocouple, an oxygen sensor, a velocity Doppler probe, an electrocardiogram (ECG) sensor, an electroencephalograph (EEG) sensor, or the like. The communication link may include an optical fiber link, a wireless, a wire link, or the like.

Carrier gas entering headgear 10B at carrier gas port 28 enters head space 89. Carrier gas flows in head space 89 from the neck toward the crown of the head, exiting at exit port 41. Headgear 10B may include a carrier gas mover, such as fan 58 of FIG. 2, that circulates carrier gas within headgear 10B. Other carrier gas movers, such as a pressurized carrier gas supply or a pump, may be used to move the carrier gas instead of or in addition to fan 58.

Figure 6:
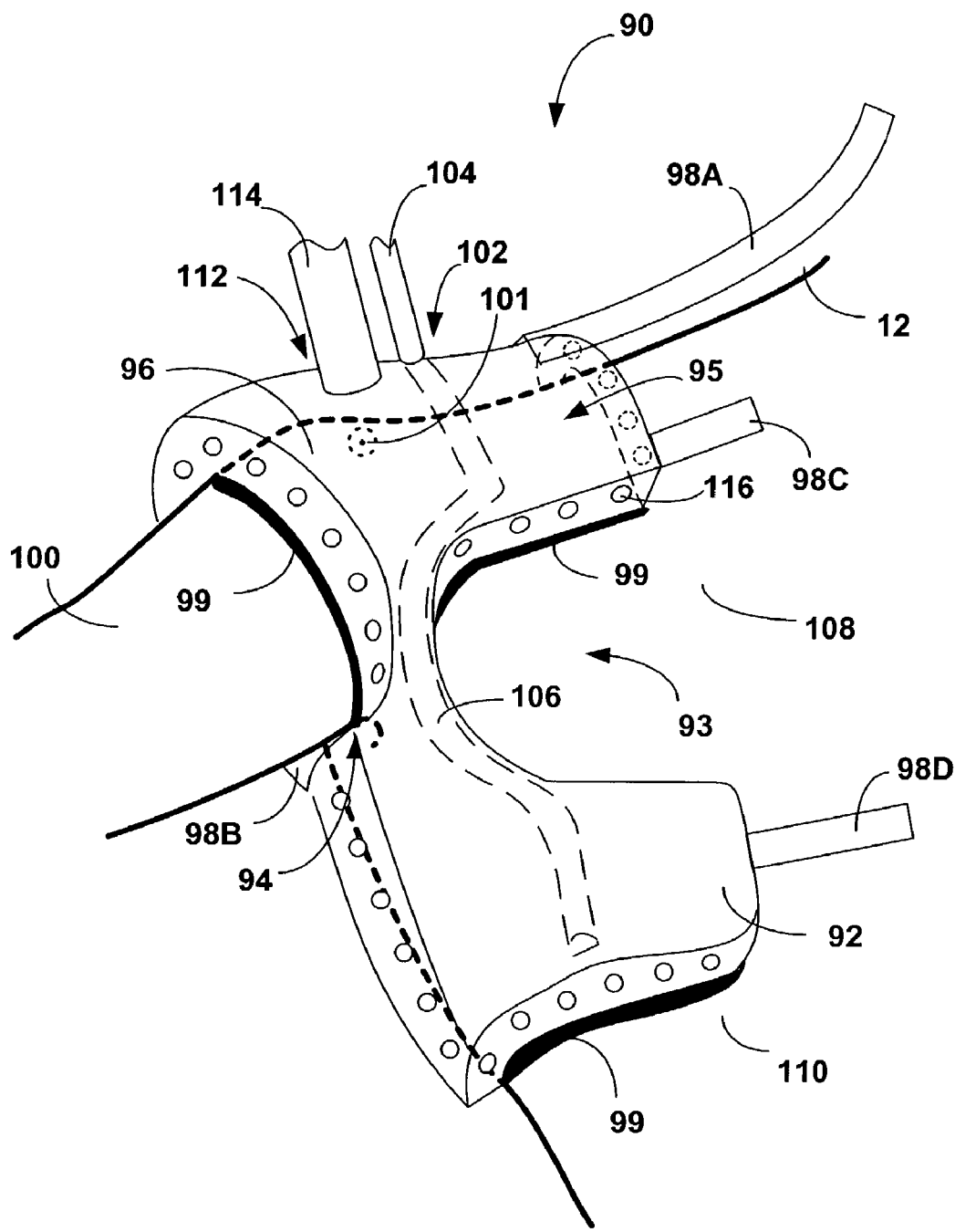
FIG. 6 is a schematic diagram illustrating a front view of an exemplary upper body gear used for cooling of a patient, according to an embodiment of the invention.

FIG. 6 is a schematic diagram illustrating a front view of an exemplary upper body gear 90 used for cooling of a patient 12. Upper body gear 90 is another embodiment of a cooling garment. Upper body gear 90 comprises a shell 92 that surrounds at least a portion of an armpit of patient 12. Shell 92 may also surround a portion of a shoulder of patient 12. Shell 92 may contain a body access 93 to allow access to or accommodate the body of patient 12. For example, body access 93 includes a U-shaped recess. The U-shaped recess may serve several functions. For example, the recess may accommodate the anatomy of a female patient. Second, the recess may allow a medical care provider to have access to the chest of the patient for purposes such as auscultation or defibrillation.

Shell 92 includes a spacer (not shown) that separates at least a portion of upper body gear 90 from the body of patient 12 defining an "upper body space" 95. Fasteners 98A–98D (collectively fasteners 98) secure shell 92 to the body of patient 12. Although in the example of FIG. 5 four fasteners secure shell 92 to patient 12, more or fewer fasteners may secure upper body gear 90.

Fasteners 98 adjust to fit upper body gear 90 on bodies of varying shapes and sizes. Fastener 98A may fasten upper body gear 90 from shoulder 96 to neck area 40 of headgear 10. Fastener 98A may keep upper body gear 90 from sliding down arm 100 of patient 12. Fastener 98B may tighten upper body gear 90 around armpit 94 of patient 12. Fastener 98B may bring upper body gear 90 in closer contact with armpit 94 in order to increase the efficiency of the cooling process. Fasteners 98C and 98D may stretch across the chest of patient 12 and couple to an upper body gear that surrounds the armpit area on the other side of the body of patient 12. Fasteners 98 draw one or more sealing members 99 in contact the body of patient 12, substantially isolating upper body space 95 created by the spacer inside of body gear 90 from an external environment. Fasteners 98 may be any sort of fastening device such as a zipper, a hook and loop fastener such as VELCRO, an adhesive, a button, a clip, a strap, a buckle or the like. Shell 92 may be constructed of flexible material that may conform to the shape of the body of patient 12. Shell 92 may further be constructed of an outer material and an inner material. Outer material of shell 92 may be material such as canvas or the like. Inner material of shell 92 may be material such as vinyl liner or the like.

The spacers of upper body gear 90 may include at least one sensor 101 and a communication link (not shown). Sensor 101 generates a signal as a function of a patient parameter such as temperature, oxygen saturation levels, blood flow, heart rate or the like. The communication link may relay the signal to a processor for processing. Sensor 101 and the communication link may be housed in the spacer, in the same fashion as in headgear 10B of FIG. 2. Upper body gear 90 may further comprise a housing (not shown) to house the processor. Alternatively, the processor may also be external to upper body gear 90. Upper body gear 90 may relay the signal obtained by sensor 101 in upper body gear 90 to the same processor as the signal from sensor 54 of headgear 10. Alternatively, upper body gear 90 may relay the signal obtained by sensor 101 of upper body gear 90 to a separate processor as signals from sensor 54 of headgear 10. Sensor 101 may be any of several sensor devices such as a temperature sensor, a thermocouple, an oxygen sensor, a velocity Doppler probe, an electrocardiogram (ECG) sensor, or the like. The communication link may include an optic fiber link, a wireless link, wire link, or the like.

Upper body gear 90 further includes a coolant port 102 that receives a coolant supply 104. Coolant port 102 brings coolant supply 104 into fluid communication with a coolant delivery conduit 106. Coolant delivery conduit 106 of FIG. 5 runs from coolant port 102 to the upper chest 108, around the U-shaped portion encompassing the chest 108, and down to the upper abdominal area 110. Coolant delivery conduit 106, however, is not restricted to the path described. Coolant delivery conduit 106 may follow any sort of path within upper body gear 90. For example, coolant delivery conduit 106 may branch within upper body gear 90. Coolant delivery conduit 106 and coolant supply 104 conform substantially to coolant delivery conduit 38 and coolant supply 36 of headgear 10.

Small apertures in coolant delivery conduit 106 may allow the coolant to drip out, seep out, mist out, spray out, or otherwise exit the lumen of coolant delivery conduit 106. The coolant exits from coolant delivery conduit 106, and an absorbent layer in contact with the body of patient 12 may absorb the coolant. Heat drawn from the direct contact of the coolant and patient 12 may cause the coolant to change from a liquid state to a gaseous state.

Upper body gear 90 further includes a carrier gas port 112 that receives a carrier gas supply 114. Carrier gas port 112 brings carrier gas supply 114 into fluid communication with upper body space 95. Carrier gas supply 114 may include a coupling (not shown) that mates to carrier gas port 112. Carrier gas supply 114 may be constructed of tube-like structures made of materials such as rubber, plastic, or the like.

Carrier gas from carrier gas supply 114 enters upper body space 95 of upper body gear 90 via gas port 112. A carrier gas mover (not shown) may cause the carrier gas to circulate within upper body space 95. Carrier gas mover may be a fan, a pressurized gas source, a pump or the like. The carrier gas circulating within upper body space 95 carries the evaporated coolant out of upper body gear 90 via one or more exit ports 116.

The example described above is a body gear that covers a single armpit. Another upper body gear 90 may be placed on the other armpit of patient 12. The invention also encompasses other arrangements of upper body gear such as a single upper body gear that covers both armpits, an upper body gear without U-shaped chest section, an upper body gear that expands across the back, an upper body gear that extends further down the arm, or the like. Upper body gear 90 may further include multiple coolant delivery conduits, multiple carrier gas intake ports, or both to allow for localized cooling of portions of the body of patient 12.

Upper body gear 90 may include a warm air supply and a warm air nozzle (not shown) to blow warm air on the hand of patient 12. Warm air may reduce shivering, shivering being counterproductive to the cooling process.

Figure 7:
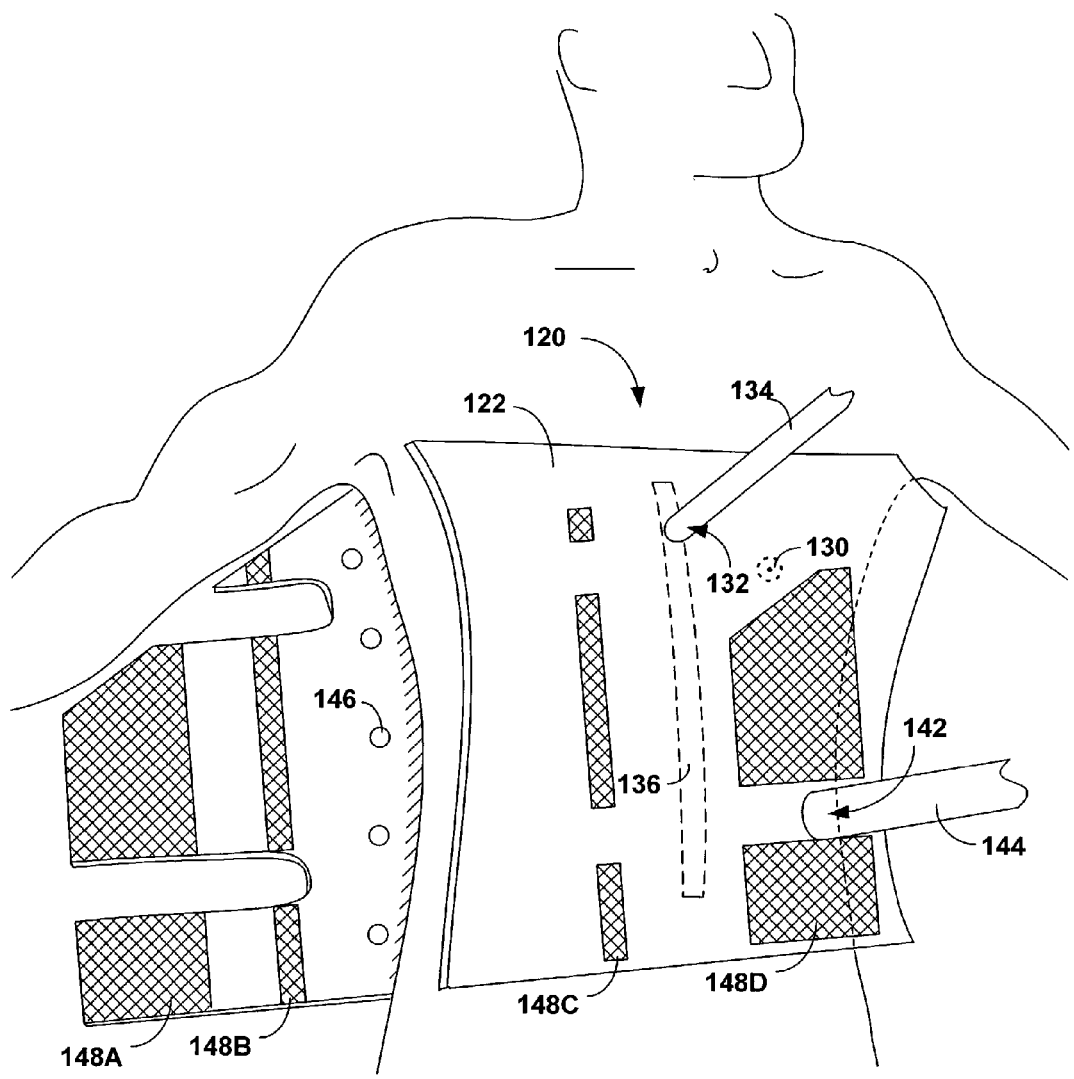
FIG. 7 is a schematic diagram illustrating a front view of another exemplary upper body gear used for cooling of a patient, according to an embodiment of the invention.

FIG. 7 is a schematic diagram illustrating a front view of another exemplary upper body gear 120 used for cooling of patient 12 Body gear 120 is another embodiment of a cooling garment. Upper body gear 120 may cool the body instead of upper body gear 90. Upper body gear 120 comprises a shell 122 that surrounds at least a portion of the torso of patient 12. Shell 122 includes a spacer (not shown) that separates at least a portion of body gear 120 from the body of patient 12 defining a "torso space" 141. Fasteners 148A–148D (collectively fasteners 148) secure shell 122 of upper body gear 120 to the body of patient 12. In the example of FIG. 7, fasteners 148 are hook and loop, e.g., VELCRO, fasteners that secure upper body gear 120 to the torso of patient 12 in an adjustable manner. For example, fasteners 148A and 148B fasten to fasteners 148C and 148D to secure upper body gear 120 to the torso of patient 12. Fasteners 148 need not be hook and loop fasteners. For example, fasteners 148 may be buttons, clips, zippers, straps, buckles or the like. Securing fasteners 148 draws a sealing member (not shown) in contact the body of patient 12, substantially isolating torso space 141 created by the spacer inside of body gear 120 from an external environment. Shell 122 may be constructed of a flexible material that may conform to the shape of the body of patient 12, and may further be constructed of an outer material and an inner material. Shell 122 may further include a body access (not shown) that allows access to or accommodates the body of patient 12. For example, shell 122 may include a body access (not shown) to accommodate the anatomy of a female patient, to allow medics to perform defibrillation, or the like.

Upper body gear 120 may include at least one sensor 130 and a communication link (not shown). Sensor 130 obtains a signal of some variable of patient 12 and the communication link may relay the signal to a processor for processing. Upper body gear 120 may further comprise a housing (not shown) to house the processor. Alternatively, the processor may also be external to upper body gear 120.

Upper body gear 120 further includes a coolant port 132 that receives a coolant supply 134. Coolant port 132 brings coolant supply 134 into fluid communication with a coolant delivery conduit 136. Coolant delivery conduit 136 runs from the chest of patient 12 to the abdomen of patient 12. Coolant delivery conduit 136, however, is not restricted to the path described. Coolant delivery conduit 136 may follow any sort of path within upper body gear 120. Coolant delivery conduit 136 may further be shaped to expand and contract to accommodate bodies of different sizes and shapes. Coolant supply 134 and coolant delivery conduit 136 conform substantially to coolant supply 36 and coolant delivery conduit 38 of headgear 10.

Small apertures in coolant delivery conduit 136 may allow the coolant to drip out, seep out, mist out, spray out, or otherwise exit the lumen of coolant delivery conduit 136. The coolant exits from coolant delivery conduit 136, and an absorbent layer (not shown) in contact with the body of patient 12 may absorb the coolant. Heat drawn from the direct contact of the coolant and patient 12 may cause the coolant to change from a liquid state to a gaseous state, i.e., to evaporate.

Upper body gear 120 further includes a carrier gas port 142 that receives a carrier gas supply 144. Carrier gas port 142 brings carrier gas supply 144 into fluid communication with torso space 141. Carrier gas supply 144 may include a coupling (not shown) that mates to carrier gas port 142. Carrier gas from carrier gas supply 144 enters torso space 141 of upper body gear 120 via carrier gas port 142. A carrier gas mover (not shown) may cause the carrier gas to circulate within torso space 141. Carrier gas mover may be a fan, a pressurized gas source, a pump or the like. The carrier gas circulating within torso space 141 carries the evaporated coolant out of upper body gear 120 via one or more of exit ports 146.

Upper body gear 120, like upper body gear 90, may allow for localized cooling of portions of the torso. Localized cooling may be accomplished using multiple coolant delivery conduits, multiple carrier gas intake ports, or both.

Figure 8:
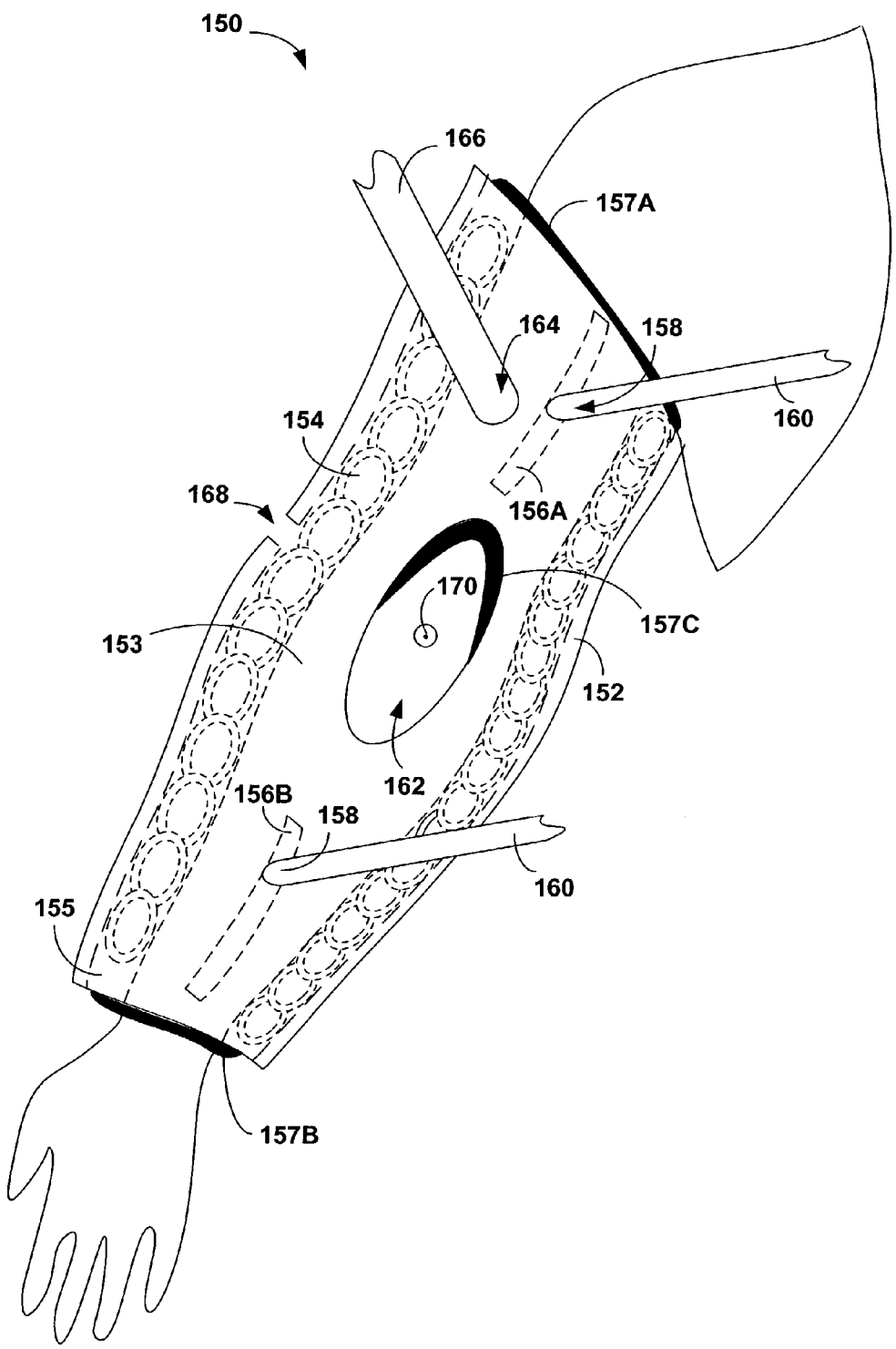
FIG. 8 is a schematic diagram illustrating a front view of another exemplary upper body gear used for cooling of a patient, according to an embodiment of the invention.

FIG. 8 is a schematic diagram illustrating a front view of another exemplary upper body gear 150 that is used to cool patient 12. Upper body gear 150 is another embodiment of a cooling garment. Upper body gear 150 may be used in conjunction with upper body gear 90 or upper body gear 120 to cool patient 12. Alternatively, upper body gear 150 may be used alone to cool patient 12. Upper body gear 150 includes a shell 152 that surrounds at least a portion of an arm 153 of patient 12. Shell 152 includes a spacer that separates at least a portion of shell 152 from arm 153 of patient 12 to create an "arm space" 155.

In the example of FIG. 7, a chain spacer 154 separates shell 152 from arm 153 of patient 12. Chain spacer 154 may be made of a lightweight material such as rubber or plastic. Chain spacer 154 need not be strong enough to bear heavy loads in compression or tension, because chain spacer 154 principally acts to create arm space 155, rather than to bear a load. The invention is not limited to use of chain spacer 154, however, and any spacer that separates at least a portion of shell 152 from the body of the patient, including an air spacer, may supplant or cooperate with chain spacer 154 to create the arm space 155. Shell 152 may be constructed of a flexible material that may conform to the shape of the body of patient 12, and may further be constructed of an outer material and an inner material.

Upper body gear 150 may further include a fastener (not shown), such as a strap or hook and loop, e.g., VELCRO, closure, which secures upper body gear 150 to the body of patient 12, and may be adjusted. Securing upper body gear 150 to patient 12 via the fasteners draws sealing members 157A–157C (collectively seal members 157) into contact with the body of patient 12. Sealing members 157 substantially isolate arm space 155 created by the spacers, such as chain spacer 154, from an external environment.

Upper body gear 150 may further include coolant delivery conduits 156A and 156B (collectively coolant delivery conduits 156) that deliver coolant to the body in arm space 155 between shell 152 and arm 153. In the example of FIG. 7, coolant delivery conduit 156A extends from the upper bicep of arm 53 to the lower bicep of patient 12, and delivers coolant to those portions of the body of patient 12. Coolant delivery conduit 156B extends across the lower portion of arm 53 of patient 12, and delivers coolant to those portions of the body of patient 12. In another embodiment, a single coolant delivery conduit may deliver coolant to the body within arm space 155. Upper body gear 150 may include coolant ports 158 that bring coolant delivery conduits 156 into fluid communication with coolant supplies 160. Small apertures in coolant delivery conduits 156 may allow the coolant to drip out, seep out, mist out, spray out, or otherwise exit the lumen of coolant delivery conduits 156. The coolant exits from coolant delivery conduit 156, and an absorbent layer (not shown) in contact with the body of patient 12 may absorb the coolant. Heat drawn from the direct contact of the coolant and patient 12 may cause the coolant to change from a liquid state to a gaseous state.

Between coolant delivery conduits 156 may be a body access 162 that allows access to a portion of the body for treatments such as intravenous drips or injections. Upper body gear 150 may include more than one body access. Another seal member 157C may be located around body access 38, to prevent leaking of coolant, carrier gas, or the like.

Upper body gear 150 further includes a carrier gas port 164 that receives a carrier gas supply 166. Carrier gas port 164 brings carrier gas supply 166 into fluid communication with arm space 155. Carrier gas from carrier gas supply 166 enters arm space 155 of upper body gear 150 via carrier gas port 164. A carrier gas mover (not shown) may cause the carrier gas to circulate within arm space 155. The carrier gas circulating within arm space 155 carries the evaporated coolant out of upper body gear 150 via one or more of exit ports 168.

Upper body gear 150 may allow for localized cooling of portions of arm 153 of patient 12 using multiple coolant delivery conduits 156, multiple carrier gas intake ports 158, or both.

Upper body gear 150 may also include at least one sensor 170 for generating a signal as a function of a patient parameter such as temperature, oxygen saturation levels, blood flow, heart rate or the like. Spacers 154 may include sensor 54. Upper body gear 150 may also include a communication link (not shown) that relays the signal from sensor 170 to a processor for processing. Upper body gear 150 may further comprise a housing (not shown) to house the processor. However, the processor may be external to upper body gear 150.

Upper body gear 150 may include a warm air supply and a warm air nozzle (not shown) to blow warm air on the hand of patient 12. Warm air may reduce shivering, shivering being counterproductive to the cooling process.

Upper body gear 150 may be constructed in two separate pieces to accommodate the placement a non-invasive blood pressure (NIBP) cuff on patient 12. A first piece may cover the upper portion of the arm and a second piece may cover the lower portion of the arm. Alternatively, the non-invasive blood pressure cuff may be included in the construction of a single piece upper body gear 150. Further, a separate upper body gear 150 may be placed on each arm of patient 12.

Figure 9:
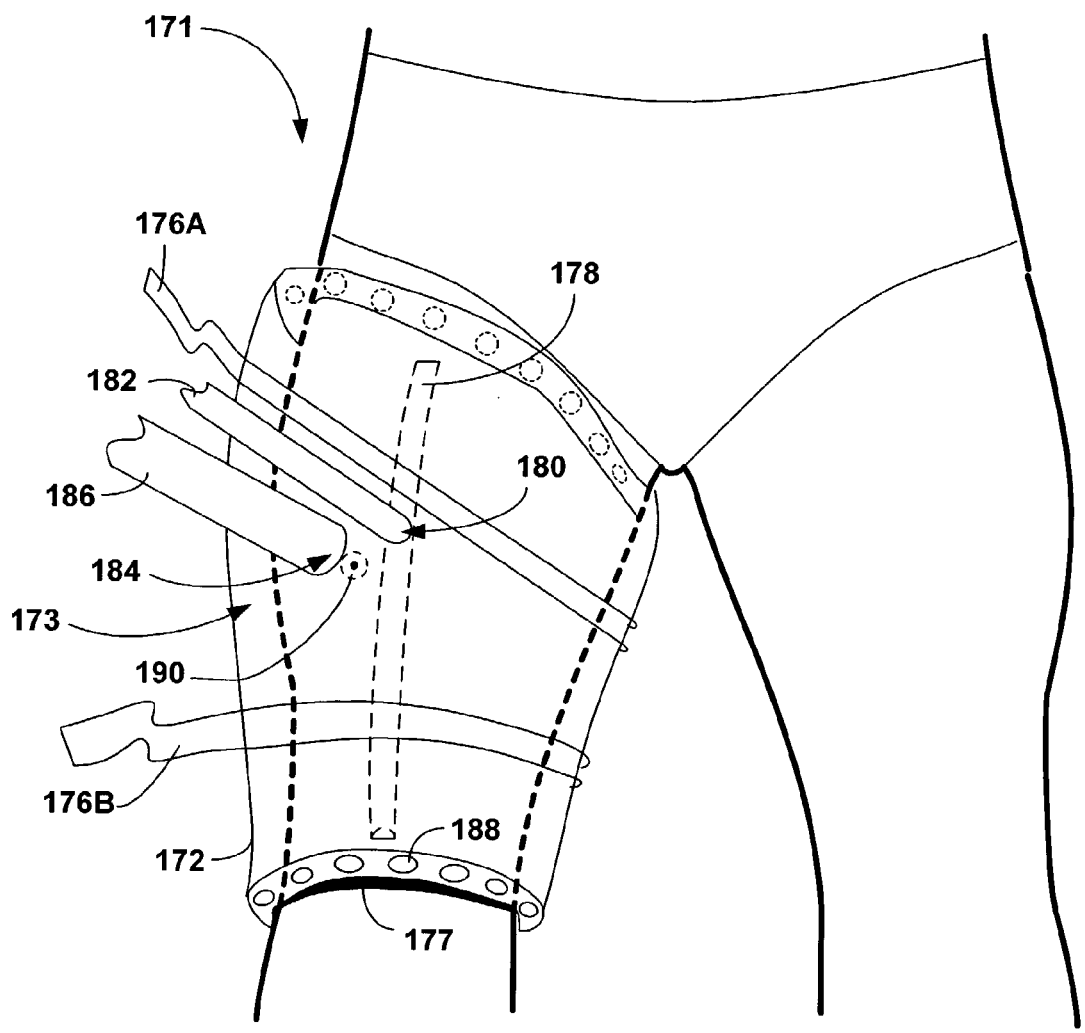
FIG. 9 is a schematic diagram illustrating a front view of an exemplary lower body gear used for cooling of a patient, according to an embodiment of the invention.

FIG. 9 is a schematic diagram illustrating a front view of an exemplary lower body gear 171 used for cooling of a patient 12. Lower body gear 171 is yet another embodiment of a cooling garment. Lower body gear 171 includes a shell 172 that surrounds at least a portion of a thigh/groin area of patient 12. Shell 172 may include spacers (not shown) that separate at least a portion of the lower body gear from the body of patient 12 defining a "lower body space" 173. Lower body gear 171 may further include fasteners 176A and 176B (collectively fasteners 176) that secure shell 172 to the body of patient 12. Fasteners 176 adjust to fit lower body gear 171 on bodies of varying shapes and sizes. For example, fastener 176A may secure lower body gear 171 about the upper thigh region, while fastener 176B may secure lower body gear 171 about the lower thigh and kneecap region. Fasteners 176 may draw a sealing member 177 in contact the body of patient 12, substantially isolating lower body space 173 created by the spacers from an external environment. Shell 172 may further include a body access (not shown) that allows access to or accommodates the body of patient 12. Shell 172 may be constructed of a flexible material that may conform to the shape of the body of patient 12, and may further be constructed of an outer material and an inner material.

Lower body gear 171 further includes a coolant delivery conduit 178 that delivers coolant to the body in lower body space 173. In the example of FIG. 8, coolant delivery conduit 178 extends from the upper thigh and groin region to the lower thigh and kneecap region. However, coolant delivery conduit may follow any sort of path within lower body gear 171. Lower body gear 171 may also include a coolant port 180 that may bring coolant delivery conduit 178 into fluid communication with a coolant supply 182. Small apertures in coolant delivery conduits 178 may allow the coolant to drip out, seep out, mist out, spray out, or otherwise exit the lumen of coolant delivery conduits 178. The coolant exits from coolant delivery conduit 178, and an absorbent layer (not shown) in contact with the body of patient 12 may absorb the coolant. Heat drawn from the direct contact of the coolant and patient 12 may cause the coolant to change from a liquid state to a gaseous state.

Lower body gear 171 further includes a carrier gas port 184 that receives a carrier gas supply 186. Carrier gas port 184 brings carrier gas supply 186 into fluid communication with lower body space 173 created by the spacers. Carrier gas supply 186 may include a coupling (not shown in FIG. 6) that mates to carrier gas port 184. Carrier gas from carrier gas supply 186 enters lower body space 173 of lower body gear 171 via carrier gas port 184. A carrier gas mover (not shown) may circulate the carrier gas within lower body space 173. The carrier gas carries the evaporated coolant out of lower body space 173 through one or more exit ports 188.

Lower body gear 171 may include at least one sensor 190 and a communication link (not shown). Sensor 190 generates a signal as a function of a patient parameter. The communication link may relay the signal to a processor for processing. The process may be internal or external to lower body gear 171. Sensor 190 may be housed within the spacers that create lower body space 173.

The example of FIG. 9 described above is a body gear that covers a single thigh and groin area. Another lower body gear 171 may be placed on the other thigh of patient 12. The invention, however, encompasses a lower body gear may be in a single thigh or groin piece. The invention further encompasses a lower body gear that may extend farther down the leg than the knee. For example, lower body gear 171 may extend to the shin or even all the way to the feet of patient 12. Lower body gear may further allow for localized cooling of the lower body of patient 12 using multiple coolant delivery conduits, multiple carrier gas intake ports, or both.

Upper body gear 150 may include a warm air supply and a warm air nozzle (not shown) to blow warm air on the feet of patient 12. Warm air may reduce shivering, shivering being counterproductive to the cooling process.

Figure 10:
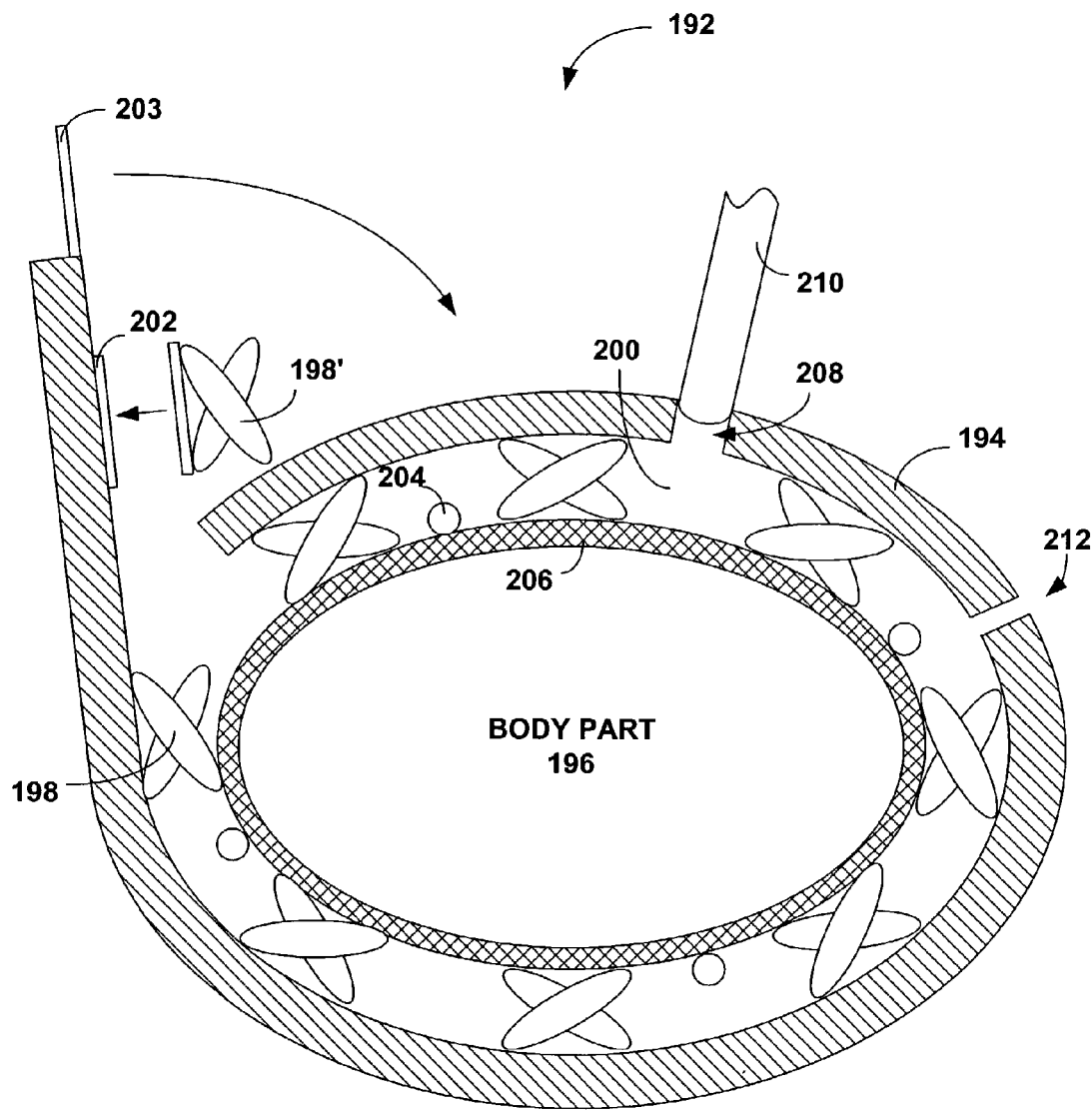
FIG. 10 is a schematic diagram illustrating a cross-sectional view of a body gear, according to an embodiment of the invention.

FIG. 10 is a schematic diagram illustrating a cross-sectional view of a body gear 192. Body gear 192 may represent any of upper body gears 90, 120, and 150 or lower body gear 171. Body gear 192 includes a shell 194 that surrounds a body part 196 of a patient 12. Shell 194 includes spacers 198, such as chain spacers, air spacers or the like that separate at least a portion of shell 194 from body part 196 creating a space 200. Some or all of spacers 198, such as spacer 198', may be attachable to and detachable from shell 194. For instance, when body gear 192 must be used for a larger body size, additional spacers 198' may be attached to attachment points 202. Attachment points 202 may be sites tat include attachment mechanisms such as hook and loop fasteners, e.g., VELCRO, adhesive or clasps. When spacers 198' are not attached to attachment points 202, the attachment point 202 may be a fastener used to secure body gear 192 to patient 12. Body gear 192 may further include a permanent fastener 203, such as a strap, that secures body gear 192 on body part 196 regardless of whether all attachment points 202 are occupied by spacer 198'.

Body gear 192 further includes one or more coolant delivery conduits 204 that deliver coolant to body part 196. Each of coolant delivery conduits 204 may be a separate coolant delivery conduit. Alternatively, each of coolant delivery conduits 204 may be a branch from a single coolant delivery conduit that follows a path within body gear 192. Coolant delivery conduit 204 may have small apertures that allow the coolant to drip out, seep out, mist out, spray out, or otherwise exit the lumen of coolant delivery conduits 204. An absorbing layer 206 may absorb the coolant that exits coolant delivery conduits 204. Absorbing layer 206 keeps the coolant in contact with body part 196 of patient 12. Heat drawn from the direct contact of the coolant and patient 12 may cause the coolant to change from a liquid state to a gaseous state.

Body gear 192 further includes a carrier gas intake port 208 that fluidly connects space 200 to a carrier gas supply 210. Carrier gas enters space 200 via carrier gas intake port 208, and circulates within space 200. The carrier gas carries the evaporated coolant from space 200 via an exit port 212.

The cooling process occurring inside of the body gear 192 is similar to that of headgear 10 described above. Space 200 within body gear 192 receives a carrier gas from carrier gas supply 210 via carrier gas port 208. Coolant delivery conduit 204 receives a coolant from a coolant supply via a coolant port.

A carrier gas mover circulates the carrier gas within space 200 of body gear 192. The liquid coolant exits the lumen of coolant conduit 204 via small apertures in coolant conduit 204. The coolant contacts the body of patient 12. The coolant may contact the body in absorbent layer 206 or may be applied directly to the body of patient 12. Heat from the body causes the coolant to evaporate. The evaporation and convection heat transfer processes cool patient 12.

The circulating carrier gas encounters evaporated coolant in space 200, and carries the coolant in gaseous form away from patient 12. The carrier gas and gaseous coolant are discharged out exit port 212 and fresh carrier gas and coolant replace what has been discharged.

Figure 11:
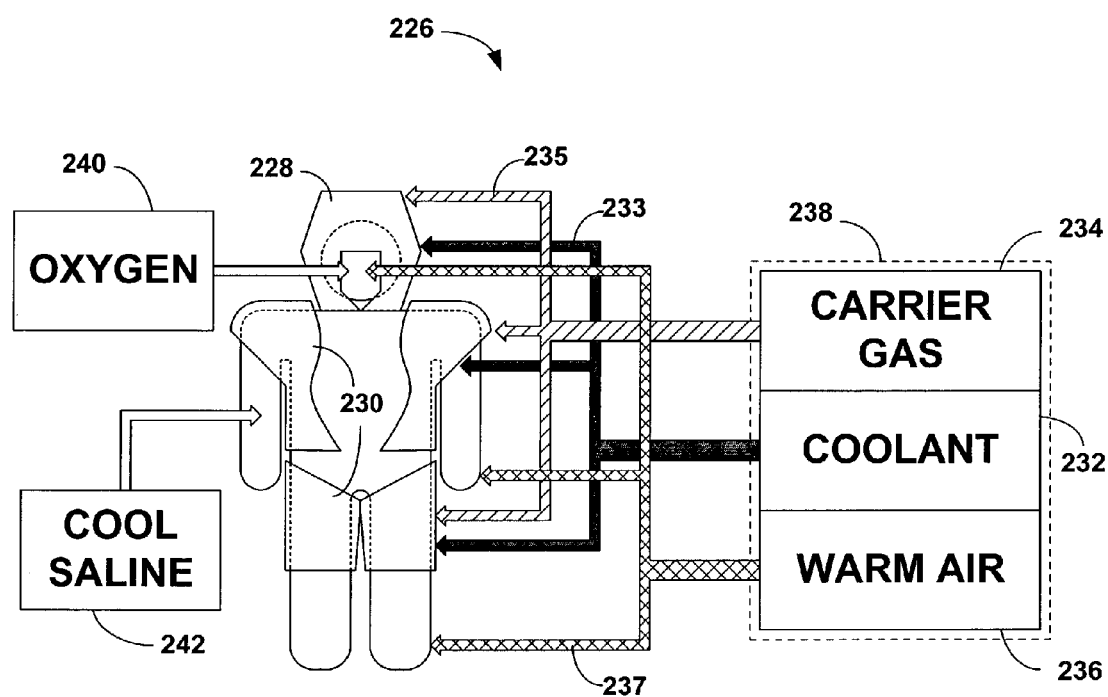
FIG. 11 is a schematic diagram illustrating a cooling system used to cool a patient, according to an embodiment of the invention.

FIG. 11 is a schematic diagram illustrating a cooling system 226 in which multiple cooling garments are used to cool a patient 12. Cooling system 226 may be applied to patient 12 after patient 12 suffers some kind of traumatic event such as stroke, cardiac arrest, head trauma or the like. Cooling system 226 may include a headgear 228, which covers at least a portion of the head of patient 12. Headgear 228 may be headgear 10A described in FIGS. 1–3, headgear 10B described in FIG. 5, or any other sort of headgear consistent with the principles of the invention.

Cooling system 226 may also include a body gear 230 that covers at least a portion of the body of patient 12. Body gear 230 may include any combination of upper body gear 90, upper body gear 120, upper body gear 150, lower body gear 171, or any other type of body gear consistent with the principles of the invention.

Both headgear 228 and body gear 230 may be constructed of materials that are sterilizable and, consequently, reusable. All or only a portion of headgear 228 and body gear 230 may be reusable. For example, an absorbent layer within headgear 228 may be replaced after every use, while all other portions of headgear 228 and body gear 230 may be sterilized and reused. Headgear 228 and body gear 230 may be sterilized using an autoclave, steam, liquid, or any other sterilization method.

Cooling system 226 may further include a coolant supply container 232. Coolant supply container 232 supplies coolant to both headgear 228 and body gear 230 via coolant supply 233. Alternatively, a separate coolant supply may supply coolant to the separate cooling pieces of cooling system 226. The coolant supplied to cooling system 226 is typically a liquid coolant such as water, alcohol, or a mixture of water and alcohol. Alternatives, however, may be used. The liquid coolant may be cooled before entering headgear 228 and body gear 230.

Cooling system 226 further includes a carrier gas supply container 234 that supplies carrier gas to both headgear 228 and body gear 230 via carrier gas supply 235. Alternatively, a separate carrier gas supply container may supply carrier gas to the separate cooling pieces of cooling system 226. Typical carrier gases include carbon dioxide, nitrogen, air, or any combination thereof. Typically, carbon dioxide and nitrogen would be stored in liquid form and expanded to a gas so as to minimize space and cool the gas supplied to headgear 228 and/or body gear 230. One or more expansion valves may be interposed between the carrier gas supply 235 and the cooling garments. Expansion valves may regulate the amount of liquid carbon dioxide or nitrogen expanded to a gas. The expansion valves may be proximate to carrier gas supply 235, or proximate to the garments so as to minimize the temperature loss as the gas flows to the cooling garments. A cooling garment may include an expansion valve. An expansion valve may be, for example, coupled to a carrier gas port of a garment.

Further, the expanded carbon dioxide or nitrogen may be mixed with air in order to adjust the temperature to a safe range for application to patient 12. The carrier gas may also be cooled by a cooling canister, such as a blue ice canister or by a heat exchanger before being supplied to cooling devices of cooling system 226. The carrier gas may further be dehumidified before entering headgear 228 and body gear 230 in order to absorb more water vapor and, in turn, enhancing the evaporative cooling process.

Cooling system 226 may also include a warm air supply container 236 to supply warm air to parts of the body not covered by cooling devices via warm air supply 237. For example, warm air supply container 236 may supply warm air to the face, hands, or feet to prevent patient 12 from shivering, which is counterproductive to the cooling process.

A container supply box 238 may include coolant supply 232, carrier gas supply 234, and warm air supply 236. Container supply box 238 may be convenient when the supplies 232, 234, 236 must be administered at the site of a traumatic event.

Cooling system may also include oxygen supply container 240 to supply oxygen to patient 12. The oxygen may be supplied to patient 12 via cannula or mask for therapeutic purposes. In some embodiments of the invention, the carrier gas is carbon dioxide, and carbon dioxide leak from the headgear in the vicinity of patient's face 20. Supplying oxygen to the patient may reduce the quantity of carbon dioxide inhaled by patient 12. Further, the oxygen may be cooled for lockout concerns.

Patient 12 may further be injected with a cool saline from cool saline container 242. For example, an infusion pump may pump cool saline into the body of patient 12 to complement the cooling process. The cool saline injected into the blood stream may increase the efficiency of the cooling process by directly cooling the blood that circulates through the body of patient 12.

The invention may provide multiple advantages. For example, the use of rapid hypothermic therapy, i.e., cooling the patient, may prevent the patient from suffering permanent brain damage. Emergency medical personnel, who are often the first to reach the patient, can administer the techniques. The cooling garments, e.g., headgear 228 and body gear 230, may further allow for hands free operation. For example, once on the body of the patient, the user may administer other treatments such as resuscitation. In addition, the cooling garments may be constructed to be light and portable in some embodiments, and may be brought to the patient at the site of the traumatic event, or at least may be contained in an ambulance. Further, the cooling garments may be sterilizable and, therefore, reusable. The cooling garments may also be powered by any source, including alternating current (AC) and direct current (DC).

Various embodiments of the invention have been described. These embodiments are illustrative of the practice of the invention. Various modifications may be made without departing from the scope of the claims. For example, a cooling garment may be constructed to include the headgear, upper body gear, and lower body gear in one full body gear. Furthermore, the cooling garments may cover other portions of the body. The cooling garments may include an air spacer, i.e., be inflatable. Other cooling techniques may complement the cooling garments. For example, the patient may breathe cool air to increase the efficiency of the cooling process or lay on a blue ice pad. Further, after cooling the patient to a defined temperature, the patient may be maintained at the desired temperature using a conduction system. For example, a cooling device may circulate cool liquid or gel that maintains the patient at the desired temperature. These and other embodiments are within the scope of the following claims.

The invention claimed is:

1. A device comprising:
 a garment configured to be placed in contact with a body;
 a spacer configured to separate at least part of the garment from the body defining a space;
 a seal member for separating the space from an exterior environment;
 a coolant delivery conduit configured to deliver a coolant to the body in the space;
 a carrier gas intake port in the garment for fluidly connecting the space to a carrier gas supply;
 an exit port in the garment for fluidly connecting the space to the exterior environment; and
 a carrier gas mover for moving the carrier gas within the space.

2. The device of claim 1, wherein the coolant is a liquid.

3. The device of claim 2, wherein the liquid coolant is one of water and alcohol.

4. The device of claim 2, wherein the liquid coolant is a mixture of water and alcohol.

5. The device of claim 1, wherein the coolant is one of a gas and a gel.

6. The device of claim 1, wherein the carrier gas from the carrier gas supply is one of carbon dioxide, nitrogen, and air.

7. The device of claim 1, wherein the carrier gas is dehumidified.

8. The device of claim 1, further comprising a fastener configured to secure the garment to the body.

9. The device of claim 8, wherein the fastener is one of a hook and loop fastener, a zipper, a button, a clip, a strap, a buckle, and an adhesive.

10. The device of claim 1, wherein the coolant delivery conduit includes at least one aperture through which the coolant exits the coolant delivery conduit.

11. The device of claim 1, wherein the carrier gas mover includes one of a fan, a pressurized gas supply, and a pump.

12. The device of claim 1, wherein the coolant delivery conduit is the seal member.

13. The device of claim 1, wherein the seal member is one of a flexible rubber web, an O-ring tube seal, and a collapsible tube.

14. The device of claim 1, further comprising a body access configured to allow access to a portion of the body.

15. The device of claim 1, wherein the spacer is coupled to the garment.

16. The device of claim 1, wherein the spacer is attachable to the garment.

17. The device of claim 1, wherein the spacer includes one of a chain and air.

18. The device of claim 1, wherein the coolant delivery conduit is the spacer.

19. The device of claim 1, further comprising an absorbent layer in contact with the body.

20. The device of claim 19, wherein the absorbent layer is constructed of one of cotton and polypropylene.

21. The device of claim 1, further comprising a support pad configured to support the body.

22. The device of claim 21, wherein the support pad is external to the cooling garment.

23. The device of claim 21, wherein the support pad is internal to the cooling garment and is absorbent.

24. The device of claim 1, further comprising a sensor generating a signal.

25. The device of claim 24, further comprising a processor for receiving the signal.

26. The device of claim 25, further comprising a communication link that communicates the signal from the sensor to the processor.

27. The device of claim 26, wherein the communication link is one of an optical fiber link, a wireless link, and a wire link.

28. The device of claim 25, further comprising a housing for the processor.

29. The device of claim 24, wherein the spacer includes the sensor.

30. The device of claim 24, further comprising a second sensor.

31. The device of claim 24, wherein the sensor is one of a temperature sensor, a thermocouple, an oxygen sensor, a velocity Doppler probe, an electrocardiogram (ECG) sensor, and an electroencephalograph (EEG) sensor.

32. The device of claim 1, further comprising an expansion valve interposed between the space and the carrier gas supply.

33. The device of claim 1, further comprising a battery pack.

34. The device of claim 1, wherein the garment is constructed of electrically insulated material.

35. The device of claim 1, wherein the garment includes a headgear configured to contact at least a portion of a head.

36. The device of claim 35, wherein the headgear further includes an inner and outer shell.

37. The device of claim 1, wherein the garment includes a body gear configured to contact at least a portion of the body.

38. The device of claim 37, wherein the body gear includes at least one of an upper body gear and a lower body gear.

39. The device of claim 38, wherein the upper body gear is configured to cover at least a portion of an armpit of the body.

40. The device of claim 38, wherein the lower body gear is configured to cover at least a portion of a groin of the body.

41. The device of claim 1, wherein the garment includes:
a headgear configured to contact at least a portion of a head; and
a body gear configured to contact at least a portion of the body.

42. A method comprising:
separating at least a portion of a cooling garment from a body of a patient with a spacer to create a space;
isolating the space between the body and the garment from an external environment via a seal member;
allowing a coolant to exit a coolant delivery conduit onto the body in the space;
allowing a carrier gas to enter the space via a carrier gas port; and
expelling the coolant in a gaseous state from an exit port in the garment.

43. The method of claim 42, wherein the coolant delivery conduit includes apertures, and wherein allowing the coolant to exit the coolant delivery conduit includes one of dripping the coolant from the apertures, misting the coolant from the apertures, seeping the coolant from the apertures, and spraying the coolant from the apertures.

44. The method of claim 42, further comprising securing the garment to the body.

45. The method of claim 44, wherein securing the garment to the body includes fastening a fastener that is coupled to the garment.

46. The method of claim 42, wherein allowing a carrier gas to enter the space via the carrier gas port further comprises allowing a carrier gas to enter the space via an expansion valve coupled to a carrier gas port.

47. The method of claim 42, further comprising circulating the carrier gas within the space via a carrier gas mover.

48. The method of claim 42, further comprising cooling at least one of the carrier gas and the coolant.

49. The method of claim 42, further comprising dehumidifying the carrier gas.

50. The method of claim 42, further comprising evaporating the coolant with heat from the body.

51. The method of claim 42, further comprising absorbing the coolant that is delivered to the body with an absorbent layer.

52. The method of claim 42, further comprising allowing access to the body of the patient via a body access in the garment.

53. The method of claim 42, further comprising:
generating a signal as a function of a patient parameter; and
relaying the signal to a processor via a communication link.

54. The method of claim 53, further comprising processing the signal.

55. The method of claim 42, farther comprising blowing warm air on an exposed body part of the patient.

56. The method of claim 42, further comprising injecting a cooled saline solution into the blood stream of the patient.

57. The method of claim 42, further comprising supplying oxygen to the patient.

58. The method of claim 57, further comprising cooling the supplied oxygen.

59. The method of claim 42, further comprising partitioning the space into areas, each area including a carrier gas port.

60. A device comprising:
an inner shell configured to be placed proximate to a body part of a patient, a space between the body part and the inner shell being an inner space;
an outer shell surrounding the inner shell, a space between the outer shell and the inner shell being an outer space in fluid communication with the inner space;
a seal member for forming a seal between the spaces and an exterior environment; and
an exit port formed through the inner shell and the outer shell for expelling a coolant and a gas, the gas moving from the outer space to the inner space.

61. The device of claim 60, further comprising an inner spacer configured to separate the inner shell from the body part.

62. The device of claim 60, further comprising an outer spacer for separating the inner shell from the outer shell.

63. The device of claim 60, wherein the inner shell and outer shell are deformable to conform to the body part.

64. The device of claim 60, further comprising a fastener configured to secure the inner shell to the body part.

65. The device of claim 60, further comprising:
a sensor configured to contact the body part and generate a signal; and
a processor for receiving the signal.

66. The device of claim 60, the outer shell including a coolant inlet port.

67. The device of claim 60, the outer shell including a coolant inlet port and a coolant outlet port.

68. The device of claim 60, further comprising a carrier gas intake port in fluid communication with the outer space.

69. The device of claim 68, further comprising a carrier gas mover for driving the gas from the carrier gas intake port to the exit port.

70. The device of claim 69, wherein the carrier gas mover is one of a fan, a pressurized gas source, and a pump.

71. The device of claim 60, further comprising a body access configured to allow access to the body of the patient.

72. The device of claim 60, wherein the outer shell is electrically insulated.

73. The device of claim 60, further comprising a battery pack.

74. The device of claim 60, further comprising an expander configured to fit the device on different size bodies.

75. The device of claim 60, further comprising a cavity for housing a processor.

76. A device comprising:
a garment configured to be placed in contact with a body;
a spacer configured to separate at least part of the garment from the body defining a space;
a coolant delivery conduit configured to deliver a coolant to the body in the space;

a carrier gas intake port in the garment for fluidly connecting the space to a carrier gas supply;

an exit port in the garment for fluidly connecting the space to the exterior environment;

a carrier gas mover for moving the carrier gas within the space; and a support pad configured to support the body, wherein the support pad is internal to the garment and is absorbent.

77. A device comprising:

a garment configured to be placed in contact with a body;

a spacer configured to separate at least part of the garment from the body defining a space;

a coolant delivery conduit configured to deliver a coolant to the body in the space;

a carrier gas intake port in the garment for fluidly connecting the space to a carrier gas supply;

an exit port in the garment for fluidly connecting the space to the exterior environment;

a carrier gas mover for moving the carrier gas within the space; and a sensor generating a signal, wherein the spacer includes the sensor.

78. The device of claim 77, further comprising a processor for receiving the signal.

79. The device of claim 78, further comprising a communication link that communicates the signal from the sensor to the processor.

80. The device of claim 79, wherein the communication link is one of an optical fiber link, a wireless link, and a wire link.

81. The device of claim 78, further comprising a housing for the processor.

82. The device of claim 77, further comprising a second sensor.

83. The device of claim 77, wherein the sensor is one of a temperature sensor, a thermocouple, an oxygen sensor, a velocity Doppler probe, an electrocardiogram (ECG) sensor, and an electroencephalograph (EEG) sensor.

* * * * *

UNITED STATES PATENT AND TRADEMARK OFFICE
CERTIFICATE OF CORRECTION

PATENT NO. : 7,179,279 B2  
APPLICATION NO. : 10/262604  
DATED : February 20, 2007  
INVENTOR(S) : Stephen W. Radons et al.

Page 1 of 1

It is certified that error appears in the above-identified patent and that said Letters Patent is hereby corrected as shown below:

On the Title page, in item (56), under "Other Publications", in column 2, line 1, delete "Internartional" and insert -- International --, therefor.

In column 11, line 18, delete "12 Body" and insert -- 12. Body --, therefor.

In column 15, line 10, delete "tat" and insert -- that --, therefor.

In column 20, line 5, in Claim 55, delete "farther" and insert -- further --, therefor.

Signed and Sealed this

Eighth Day of December, 2009

David J. Kappos
*Director of the United States Patent and Trademark Office*